US008267979B2

(12) United States Patent
Flynn et al.

(10) Patent No.: US 8,267,979 B2
(45) Date of Patent: *Sep. 18, 2012

(54) LOAD-SHARING BONE ANCHOR HAVING A DEFLECTABLE POST AND AXIAL SPRING AND METHOD FOR DYNAMIC STABILIZATION OF THE SPINE

(75) Inventors: John J. Flynn, Walnut Creek, CA (US); Charles J. Winslow, Walnut Creek, CA (US); Steven T. Mitchell, Pleasant Hill, CA (US); James F. Zucherman, San Francisco, CA (US); Ken Y. Hsu, San Francisco, CA (US); Henry A. Klyce, Piedmont, CA (US); H. Adam R. Klyce, Berkeley, CA (US)

(73) Assignee: Spartek Medical, Inc., Concord, CA (US)

( * ) Notice: Subject to any disclaimer, the term of this patent is extended or adjusted under 35 U.S.C. 154(b) by 561 days.

This patent is subject to a terminal disclaimer.

(21) Appl. No.: 12/566,559

(22) Filed: Sep. 24, 2009

(65) Prior Publication Data

US 2010/0030279 A1  Feb. 4, 2010

Related U.S. Application Data

(63) Continuation-in-part of application No. 12/130,395, filed on May 30, 2008, now Pat. No. 8,070,775, and a continuation-in-part of application No. 12/130,095, filed on May 30, 2008.

(60) Provisional application No. 61/100,593, filed on Sep. 26, 2008, provisional application No. 61/100,625, filed on Sep. 26, 2008, provisional application No. 61/119,651, filed on Dec. 3, 2008, provisional application No. 61/122,658, filed on Dec. 15, 2008, provisional application No. 61/144,426, filed on Jan. 13, 2009, provisional application No. 61/225,478, filed on Jul. 14, 2009, provisional application No. 61/167,789, filed on Apr. 8, 2009, provisional application No. 61/217,556, filed on Jun. 1, 2009, provisional application No. 61/031,598, filed on Feb. 26, 2008, provisional application No. 61/057,340, filed on May 30, 2008.

(51) Int. Cl.
*A61B 17/86* (2006.01)
(52) U.S. Cl. ...................................................... 606/305
(58) Field of Classification Search .................. 606/246, 606/279, 86 A, 272, 287, 294, 104, 96, 99, 606/289, 280, 86 R, 305, 309; 81/452, 453
See application file for complete search history.

(56) References Cited

U.S. PATENT DOCUMENTS 4,041,939 A   8/1977   Hall ............................... 128/69
(Continued)

FOREIGN PATENT DOCUMENTS

DE   2649042 B1   10/1976
(Continued)

OTHER PUBLICATIONS

International Search Report for PCT/US2010/058776 dated Aug. 23, 2011, 4 pages.

(Continued)

*Primary Examiner* — Pedro Philogene
(74) *Attorney, Agent, or Firm* — Fliesler Meyer LLP

(57) ABSTRACT

A dynamic spinal stabilization component which supports the spine while providing for the preservation of spinal motion. The component may be integrated in a bone anchor for implantation in a bone of the spine. The component and bone anchor provide load sharing while preserving range of motion and reducing stress exerted upon the bone anchors and spinal anatomy. The dynamic spinal stabilization component includes a deflectable post connected by a ball-joint to a threaded anchor. Deflection of the deflectable post is controlled by an axially compressible spring. The force/deflection properties of the dynamic bone anchor may be adapted to the anatomy and functional requirements of the patient. The dynamic spinal stabilization component may be used as a component of a dynamic stabilization system which supports the spine while providing for the preservation of spinal motion.

25 Claims, 11 Drawing Sheets

U.S. PATENT DOCUMENTS

| | | | |
|---|---|---|---|
| 4,065,817 A | 1/1978 | Branemark et al. | 3/1.91 |
| 4,274,401 A | 6/1981 | Miskew | |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,116,334 A | 5/1992 | Cozad et al. | |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,374,267 A | 12/1994 | Siegal | |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,480,442 A | 1/1996 | Bertagnoli | |
| 5,487,742 A | 1/1996 | Cotrel | 606/61 |
| 5,496,321 A | 3/1996 | Puno et al. | 606/61 |
| 5,498,264 A | 3/1996 | Schlapfer et al. | 606/72 |
| 5,501,684 A | 3/1996 | Schlapfer et al. | |
| 5,520,689 A | 5/1996 | Schläpfer et al. | 606/61 |
| 5,534,001 A | 7/1996 | Schlapfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A | 10/1996 | Graf | 623/17 |
| 5,569,248 A | 10/1996 | Mathews | 606/61 |
| 5,591,166 A | 1/1997 | Bernhardt et al. | |
| 5,601,552 A | 2/1997 | Cotrel | |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,658,285 A | 8/1997 | Marnay et al. | |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,310 A | 10/1997 | Yuan et al. | |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |

| Patent No. | Date | Inventor | Class |
|---|---|---|---|
| 5,800,435 A | 9/1998 | Errico et al. | 606/61 |
| 5,810,819 A | 9/1998 | Errico et al. | 606/61 |
| 5,863,293 A | 1/1999 | Richelsoph | 606/61 |
| 5,868,745 A | 2/1999 | Alleyne | |
| 5,879,350 A | 3/1999 | Sherman et al. | 606/61 |
| 5,885,286 A | 3/1999 | Sherman et al. | 606/61 |
| 5,891,145 A | 4/1999 | Morrison et al. | 606/61 |
| 5,899,904 A | 5/1999 | Errico et al. | 606/61 |
| RE36,221 E | 6/1999 | Breard et al. | 606/61 |
| 5,910,142 A | 6/1999 | Tatar | 606/61 |
| 5,925,047 A | 7/1999 | Errico et al. | 606/61 |
| 5,928,231 A | 7/1999 | Klein et al. | 606/65 |
| 5,928,232 A | 7/1999 | Howland et al. | 606/61 |
| 5,928,233 A | 7/1999 | Apfelbaum et al. | 606/61 |
| 5,947,965 A | 9/1999 | Bryan | 606/61 |
| 5,947,969 A | 9/1999 | Errico et al. | 606/61 |
| 5,954,725 A | 9/1999 | Sherman et al. | 606/78 |
| 5,961,517 A | 10/1999 | Biedermann et al. | 606/61 |
| 5,964,760 A | 10/1999 | Richelsoph | 606/61 |
| 5,980,521 A | 11/1999 | Montague et al. | 606/61 |
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,033,410 A | 3/2000 | McLean et al. | |
| 6,036,693 A | 3/2000 | Yuan et al. | 606/61 |
| 6,050,997 A * | 4/2000 | Mullane | 606/250 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,123,706 A | 9/2000 | Lange | |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,132,464 A | 10/2000 | Martin | |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,267,765 B1 | 7/2001 | Taylor et al. | |
| 6,273,888 B1 | 8/2001 | Justis | 606/61 |
| 6,273,914 B1 | 8/2001 | Papas | 623/17.11 |
| 6,280,442 B1 | 8/2001 | Barker et al. | |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,882 B1 | 10/2001 | Lin et al. | |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schäffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,475,219 B1 | 11/2002 | Shelokov | |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,831 B1 | 4/2003 | Rivard et al. | |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,589,243 B1 | 7/2003 | Viart et al. | |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,676,661 B1 | 1/2004 | Martin Benlloch et al. | |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,740,086 B2 | 5/2004 | Richelsoph | |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,827,743 B2 | 12/2004 | Eisermann et al. | |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,029 B2 | 2/2005 | Yeh | |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht | 128/898 |
| 6,887,242 B2 * | 5/2005 | Doubler et al. | 606/274 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |

| Patent | Type | Date | Inventor(s) | Class |
|---|---|---|---|---|
| 7,018,378 | B2 | 3/2006 | Biedermann et al. | 606/61 |
| 7,018,379 | B2 | 3/2006 | Drewry | 606/61 |
| 7,022,122 | B2 | 4/2006 | Amrein et al. | 606/61 |
| 7,029,475 | B2 | 4/2006 | Panjabi | 606/61 |
| 7,033,392 | B2 | 4/2006 | Schmiel | |
| 7,048,736 | B2 | 5/2006 | Robinson et al. | 606/61 |
| 7,051,451 | B2 | 5/2006 | Augostino et al. | 33/512 |
| 7,060,066 | B2 | 6/2006 | Zhao et al. | 606/61 |
| 7,074,237 | B2 | 7/2006 | Goble et al. | 623/17.11 |
| 7,081,117 | B2 | 7/2006 | Bono et al. | 606/61 |
| 7,083,621 | B2 | 8/2006 | Shaolian et al. | 606/61 |
| 7,083,622 | B2 | 8/2006 | Simonson | 606/61 |
| 7,087,056 | B2 | 8/2006 | Vaughan | 606/61 |
| 7,087,057 | B2 | 8/2006 | Konieczynski et al. | 606/73 |
| 7,087,084 | B2 | 8/2006 | Reiley | 623/17.11 |
| 7,090,698 | B2 | 8/2006 | Goble et al. | 623/17.11 |
| 7,101,398 | B2 | 9/2006 | Dooris et al. | 623/13.11 |
| 7,104,991 | B2 | 9/2006 | Dixon | |
| 7,104,992 | B2 | 9/2006 | Bailey | 606/61 |
| 7,107,091 | B2 | 9/2006 | Jutras et al. | 600/429 |
| 7,125,410 | B2 | 10/2006 | Freudiger | 606/61 |
| 7,125,426 | B2 | 10/2006 | Moumene et al. | 623/23.42 |
| 7,137,985 | B2 | 11/2006 | Jahng | |
| 7,163,538 | B2 * | 1/2007 | Altarac et al. | 606/86 A |
| 7,189,235 | B2 | 3/2007 | Cauthen | |
| 7,214,227 | B2 | 5/2007 | Colleran et al. | 606/61 |
| 7,250,052 | B2 | 7/2007 | Landry et al. | 606/61 |
| 7,270,665 | B2 | 9/2007 | Morrison et al. | |
| 7,282,064 | B2 | 10/2007 | Chin | 623/17.15 |
| 7,294,128 | B2 | 11/2007 | Alleyne et al. | |
| 7,294,129 | B2 | 11/2007 | Hawkins et al. | 606/61 |
| 7,306,603 | B2 | 12/2007 | Boehm, Jr. et al. | 606/61 |
| 7,306,606 | B2 | 12/2007 | Sasing | 606/61 |
| 7,309,355 | B2 | 12/2007 | Donnelly et al. | |
| 7,326,210 | B2 | 2/2008 | Jahng et al. | 606/61 |
| 7,335,201 | B2 * | 2/2008 | Doubler et al. | 606/264 |
| 7,338,490 | B2 | 3/2008 | Ogilvie et al. | |
| 7,338,491 | B2 | 3/2008 | Baker et al. | |
| 7,344,539 | B2 | 3/2008 | Serhan et al. | |
| 7,361,196 | B2 | 4/2008 | Fallin et al. | |
| 7,377,923 | B2 | 5/2008 | Purcell et al. | |
| 7,445,627 | B2 | 11/2008 | Hawkes et al. | |
| 7,455,684 | B2 | 11/2008 | Gradel et al. | |
| 7,476,238 | B2 | 1/2009 | Panjabi | |
| 7,479,156 | B2 | 1/2009 | Lourdel et al. | |
| 7,481,828 | B2 | 1/2009 | Mazda et al. | |
| 7,491,218 | B2 | 2/2009 | Landry et al. | |
| 7,503,924 | B2 | 3/2009 | Lee et al. | |
| 7,513,905 | B2 | 4/2009 | Jackson | |
| 7,513,911 | B2 | 4/2009 | Lambrecht et al. | |
| 7,520,879 | B2 | 4/2009 | Justis | |
| 7,530,992 | B2 | 5/2009 | Biedermann et al. | |
| 7,533,672 | B2 | 5/2009 | Morgan et al. | |
| 7,553,320 | B2 | 6/2009 | Molz, IV et al. | |
| 7,553,329 | B2 | 6/2009 | Lambrecht et al. | |
| 7,559,943 | B2 | 7/2009 | Mujwid | |
| 7,563,274 | B2 | 7/2009 | Justis et al. | |
| 7,572,279 | B2 | 8/2009 | Jackson | |
| 7,578,833 | B2 | 8/2009 | Bray | |
| 7,585,312 | B2 | 9/2009 | Rawlins et al. | |
| 7,588,575 | B2 | 9/2009 | Colleran et al. | |
| 7,588,588 | B2 | 9/2009 | Spitler et al. | |
| 7,594,924 | B2 | 9/2009 | Albert et al. | |
| 7,597,707 | B2 | 10/2009 | Freudiger | |
| 7,601,166 | B2 | 10/2009 | Biedermann et al. | |
| 7,608,095 | B2 | 10/2009 | Yuan et al. | |
| 7,611,526 | B2 | 11/2009 | Carl et al. | |
| 7,615,068 | B2 | 11/2009 | Timm et al. | |
| 7,625,394 | B2 | 12/2009 | Molz, IV et al. | |
| 7,625,396 | B2 | 12/2009 | Jackson | |
| 7,635,379 | B2 | 12/2009 | Callahan et al. | |
| 7,648,520 | B2 | 1/2010 | Markworth | |
| 7,648,522 | B2 | 1/2010 | David | |
| 7,662,172 | B2 | 2/2010 | Warnick | |
| 7,662,173 | B2 | 2/2010 | Cragg et al. | |
| 7,662,175 | B2 | 2/2010 | Jackson | |
| 7,674,293 | B2 | 3/2010 | Kuiper et al. | |
| 7,678,136 | B2 | 3/2010 | Doubler et al. | |
| 7,678,137 | B2 | 3/2010 | Butler et al. | |
| 7,682,377 | B2 | 3/2010 | Konieczynski et al. | |
| 7,691,129 | B2 | 4/2010 | Felix | |
| 7,691,132 | B2 | 4/2010 | Landry et al. | |
| 7,699,873 | B2 | 4/2010 | Stevenson et al. | |
| 7,699,875 | B2 | 4/2010 | Timm et al. | |
| 7,704,270 | B2 | 4/2010 | De Coninck | |
| 7,708,762 | B2 | 5/2010 | McCarthy et al. | |
| 7,713,287 | B2 | 5/2010 | Timm et al. | |
| 7,713,288 | B2 | 5/2010 | Timm et al. | |
| 7,717,939 | B2 | 5/2010 | Ludwig et al. | |
| 7,722,646 | B2 | 5/2010 | Ralph et al. | |
| 7,722,649 | B2 | 5/2010 | Biedermann et al. | |
| 7,722,654 | B2 | 5/2010 | Taylor et al. | |
| 7,727,259 | B2 | 6/2010 | Park | |
| 7,727,261 | B2 | 6/2010 | Barker et al. | |
| 7,731,734 | B2 * | 6/2010 | Clement et al. | 606/246 |
| 7,731,736 | B2 | 6/2010 | Guenther et al. | |
| 7,763,051 | B2 | 7/2010 | Labrom et al. | |
| 7,763,052 | B2 | 7/2010 | Jahng | |
| 7,766,944 | B2 | 8/2010 | Metz-Stavenhagen | |
| 7,766,945 | B2 | 8/2010 | Nilsson et al. | |
| 7,776,071 | B2 | 8/2010 | Fortin et al. | |
| 7,785,350 | B2 | 8/2010 | Eckhardt et al. | |
| 7,785,354 | B2 | 8/2010 | Biedermann et al. | |
| 7,789,896 | B2 | 9/2010 | Jackson | |
| 7,794,477 | B2 | 9/2010 | Melkent et al. | |
| 7,794,481 | B2 | 9/2010 | Molz, IV et al. | |
| 7,799,060 | B2 | 9/2010 | Lange et al. | |
| 7,803,189 | B2 | 9/2010 | Koske | |
| 7,806,913 | B2 | 10/2010 | Fanger et al. | |
| 7,806,914 | B2 | 10/2010 | Boyd et al. | |
| 7,811,288 | B2 | 10/2010 | Jones et al. | |
| 7,811,309 | B2 | 10/2010 | Timm et al. | |
| 7,811,311 | B2 | 10/2010 | Markworth et al. | |
| 7,815,664 | B2 | 10/2010 | Sherman et al. | |
| 7,815,665 | B2 | 10/2010 | Jahng et al. | |
| 7,819,899 | B2 | 10/2010 | Lancial | |
| 7,819,901 | B2 | 10/2010 | Yuan et al. | |
| 7,819,902 | B2 | 10/2010 | Abdelgany et al. | |
| 7,828,824 | B2 | 11/2010 | Kwak et al. | |
| 7,828,825 | B2 | 11/2010 | Bruneau et al. | |
| 7,828,826 | B2 | 11/2010 | Drewry et al. | |
| 7,828,830 | B2 | 11/2010 | Thramann et al. | |
| 7,833,250 | B2 | 11/2010 | Jackson | |
| 7,833,256 | B2 | 11/2010 | Biedermann et al. | |
| 7,842,072 | B2 | 11/2010 | Dawson | |
| 7,850,715 | B2 | 12/2010 | Banouskou et al. | |
| 7,850,718 | B2 * | 12/2010 | Bette et al. | 606/267 |
| 7,854,752 | B2 | 12/2010 | Colleran et al. | |
| 7,857,833 | B2 | 12/2010 | Abdou | |
| 7,857,834 | B2 | 12/2010 | Boschert | |
| 7,862,586 | B2 | 1/2011 | Malek | |
| 7,862,587 | B2 | 1/2011 | Jackson | |
| 7,862,588 | B2 | 1/2011 | Abdou | |
| 7,862,591 | B2 | 1/2011 | Dewey et al. | |
| 7,862,594 | B2 | 1/2011 | Abdelgany et al. | |
| 7,871,413 | B2 | 1/2011 | Park et al. | |
| 7,875,059 | B2 | 1/2011 | Patterson et al. | |
| 7,875,060 | B2 | 1/2011 | Chin | |
| 7,879,074 | B2 | 2/2011 | Kwak et al. | |
| 7,892,266 | B2 | 2/2011 | Carli | |
| 7,909,856 | B2 | 3/2011 | Yuan et al. | |
| 7,914,558 | B2 | 3/2011 | Landry et al. | |
| 7,918,792 | B2 | 4/2011 | Drzyzga et al. | |
| 7,927,359 | B2 | 4/2011 | Trautwein | |
| 7,942,910 | B2 | 5/2011 | Doubler et al. | |
| 8,057,515 | B2 * | 11/2011 | Flynn et al. | 606/246 |
| 8,057,517 | B2 * | 11/2011 | Flynn et al. | 606/257 |
| 8,083,775 | B2 * | 12/2011 | Winslow et al. | 606/264 |
| 8,097,024 | B2 * | 1/2012 | Winslow et al. | 606/264 |
| 2003/0004511 | A1 | 1/2003 | Ferree | |
| 2003/0171749 | A1 | 9/2003 | Le Couedic et al. | |
| 2004/0015166 | A1 | 1/2004 | Gorek | |
| 2004/0034374 | A1 | 2/2004 | Zatzsch et al. | |
| 2004/0049285 | A1 | 3/2004 | Haas | |
| 2004/0097925 | A1 | 5/2004 | Boehm, Jr. et al. | |
| 2004/0111088 | A1 | 6/2004 | Picetti et al. | |
| 2004/0122425 | A1 | 6/2004 | Suzuki et al. | |
| 2004/0147928 | A1 | 7/2004 | Landry et al. | |

| | | |
|---|---|---|
| 2004/0153077 A1 | 8/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172024 A1 | 9/2004 | Gorek |
| 2004/0215192 A1 | 10/2004 | Justis et al. |
| 2004/0225289 A1 | 11/2004 | Biedermann et al. |
| 2004/0230192 A1 | 11/2004 | Graf |
| 2004/0230304 A1 | 11/2004 | Yuan et al. |
| 2005/0049589 A1 | 3/2005 | Jackson |
| 2005/0080415 A1 | 4/2005 | Keyer et al. |
| 2005/0090822 A1 | 4/2005 | DiPoto |
| 2005/0096652 A1 | 5/2005 | Burton |
| 2005/0107788 A1 | 5/2005 | Beaurain et al. |
| 2005/0113923 A1 | 5/2005 | Acker et al. |
| 2005/0131404 A1 | 6/2005 | Mazda et al. |
| 2005/0131406 A1 | 6/2005 | Reiley et al. |
| 2005/0143737 A1 | 6/2005 | Pafford et al. |
| 2005/0171537 A1 | 8/2005 | Mazel et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0182400 A1 | 8/2005 | White |
| 2005/0182401 A1 | 8/2005 | Timm et al. |
| 2005/0192569 A1 | 9/2005 | Nichols et al. |
| 2005/0228382 A1 | 10/2005 | Richelsoph et al. |
| 2005/0228385 A1 | 10/2005 | Iott et al. |
| 2005/0240180 A1 | 10/2005 | Vienney et al. |
| 2005/0240265 A1 | 10/2005 | Kuiper et al. |
| 2005/0261770 A1 | 11/2005 | Kuiper et al. |
| 2005/0267470 A1 | 12/2005 | McBride |
| 2005/0277922 A1 | 12/2005 | Trieu et al. |
| 2005/0288670 A1 | 12/2005 | Panjabi et al. |
| 2006/0025771 A1 | 2/2006 | Jackson |
| 2006/0036324 A1 | 2/2006 | Sachs et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058787 A1 | 3/2006 | David |
| 2006/0058788 A1 | 3/2006 | Hammer et al. |
| 2006/0079894 A1 | 4/2006 | Colleran et al. |
| 2006/0079896 A1 | 4/2006 | Kwak et al. |
| 2006/0084978 A1 | 4/2006 | Mokhtar |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084990 A1 | 4/2006 | Gournay et al. |
| 2006/0085069 A1 | 4/2006 | Kim |
| 2006/0085070 A1 | 4/2006 | Kim |
| 2006/0089643 A1 | 4/2006 | Mujwid |
| 2006/0095035 A1 | 5/2006 | Jones et al. |
| 2006/0106383 A1 | 5/2006 | Biedermann et al. |
| 2006/0111712 A1 | 5/2006 | Jackson |
| 2006/0122620 A1 | 6/2006 | Kim |
| 2006/0129148 A1 | 6/2006 | Simmons et al. |
| 2006/0129149 A1 | 6/2006 | Iott et al. |
| 2006/0142761 A1 | 6/2006 | Landry et al. |
| 2006/0149242 A1 | 7/2006 | Kraus et al. |
| 2006/0149244 A1 | 7/2006 | Amrein et al. |
| 2006/0149380 A1 | 7/2006 | Lotz et al. |
| 2006/0161153 A1 | 7/2006 | Hawkes et al. |
| 2006/0195093 A1 | 8/2006 | Jahng |
| 2006/0200128 A1 | 9/2006 | Mueller |
| 2006/0200131 A1 | 9/2006 | Chao et al. |
| 2006/0229607 A1 | 10/2006 | Brumfield |
| 2006/0229613 A1 | 10/2006 | Timm et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247631 A1 | 11/2006 | Ahn et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0016190 A1 | 1/2007 | Martinez et al. |
| 2007/0016194 A1 | 1/2007 | Shaolian et al. |
| 2007/0016201 A1 | 1/2007 | Freudiger |
| 2007/0049936 A1 | 3/2007 | Colleran et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0118122 A1 | 5/2007 | Butler et al. |
| 2007/0123871 A1 | 5/2007 | Jahng |
| 2007/0161994 A1 | 7/2007 | Lowery et al. |
| 2007/0162007 A1 | 7/2007 | Shoham |
| 2007/0167946 A1 | 7/2007 | Triplett et al. |
| 2007/0167947 A1 | 7/2007 | Gittings |
| 2007/0198014 A1 | 8/2007 | Graf et al. |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0250061 A1 | 10/2007 | Chin et al. |
| 2007/0270836 A1 | 11/2007 | Bruneau et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |
| 2008/0183215 A1 | 7/2008 | Altarac et al. |
| 2008/0195208 A1 | 8/2008 | Castellvi et al. |
| 2008/0262554 A1 | 10/2008 | Hayes et al. |
| 2008/0312693 A1 | 12/2008 | Trautwein et al. |
| 2009/0062868 A1 | 3/2009 | Casutt |
| 2010/0174317 A1 | 7/2010 | Timm et al. |
| 2010/0198270 A1 | 8/2010 | Barker et al. |
| 2010/0222819 A1 | 9/2010 | Timm et al. |

FOREIGN PATENT DOCUMENTS

| | | |
|---|---|---|
| DE | 3639810 A1 | 5/1988 |
| EP | 0128058 B1 | 4/1988 |
| EP | 0669109 B1 | 8/1995 |
| EP | 0982007 | 3/2000 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2844180 A1 | 3/2004 |
| FR | 2880256 B1 | 7/2006 |
| GB | 780652 | 8/1957 |
| GB | 2173104 | 10/1986 |
| GB | 2382304 | 5/2003 |
| KR | 20080072848 | 8/2008 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |

| | | |
|---|---|---|
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO2004/024011 | 3/2004 |
| WO | WO2004/034916 | 4/2004 |
| WO | WO2006/033503 | 3/2006 |
| WO | WO2006/066685 | 6/2006 |
| WO | WO2006/105935 | 10/2006 |
| WO | WO2007064324 | 6/2007 |
| WO | WO2007/080317 | 7/2007 |
| WO | WO2008/034130 | 3/2008 |
| WO | WO2008/073544 | 6/2008 |

OTHER PUBLICATIONS

Mekanika, Inc. Website, 2003; Mekanika—The Spinal Stabilization Company, product description for Modulus System, 2 pages, <http://mekanika.com/htm/modsystem.htm>.

Zimmer, Inc. Website, 2007; Zimmer Spine, product description for Dynesis—The Dynamic Stabilization System, 5 pages, <http://www.zimmer.com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

International Search Report dated May 8, 2012 for Application No. PCT/US2011/057403, 17 pages.

\* cited by examiner

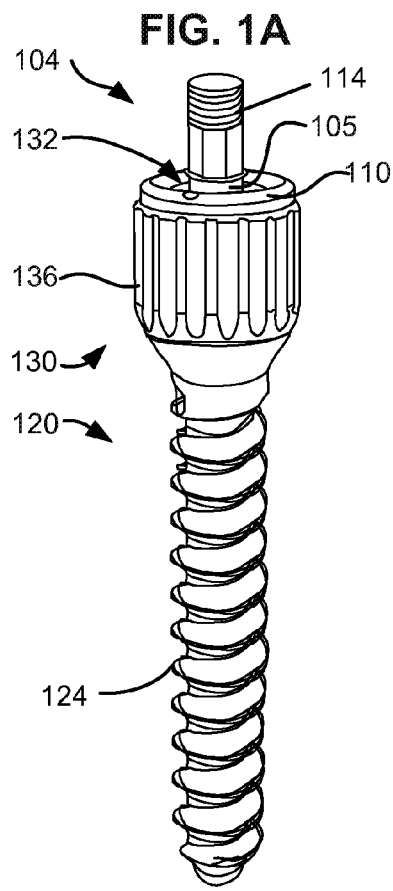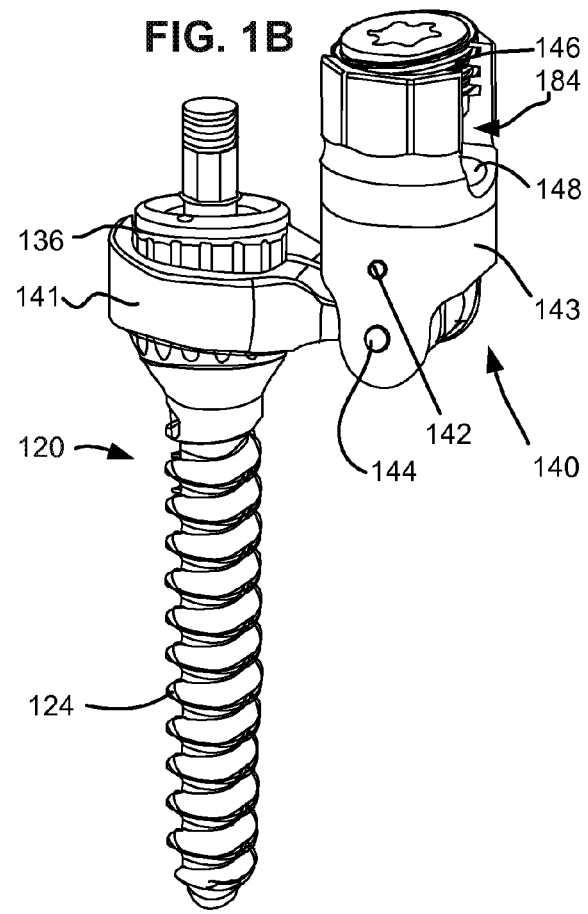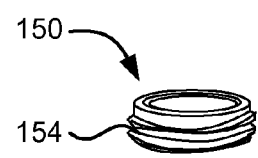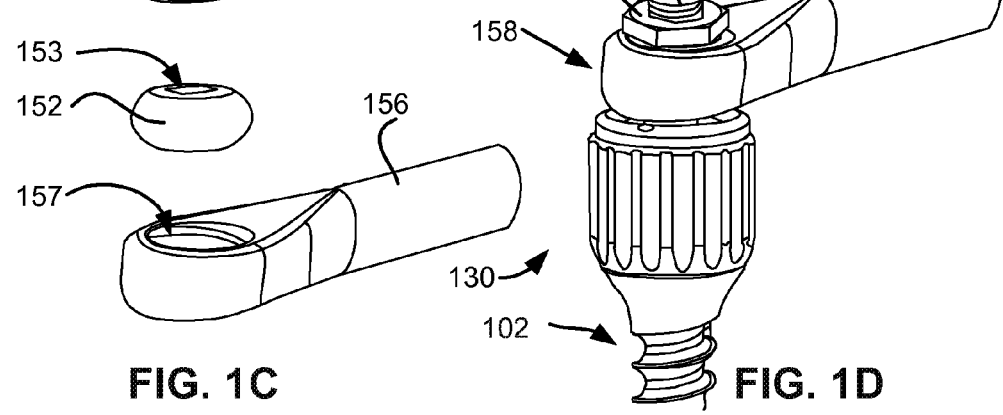

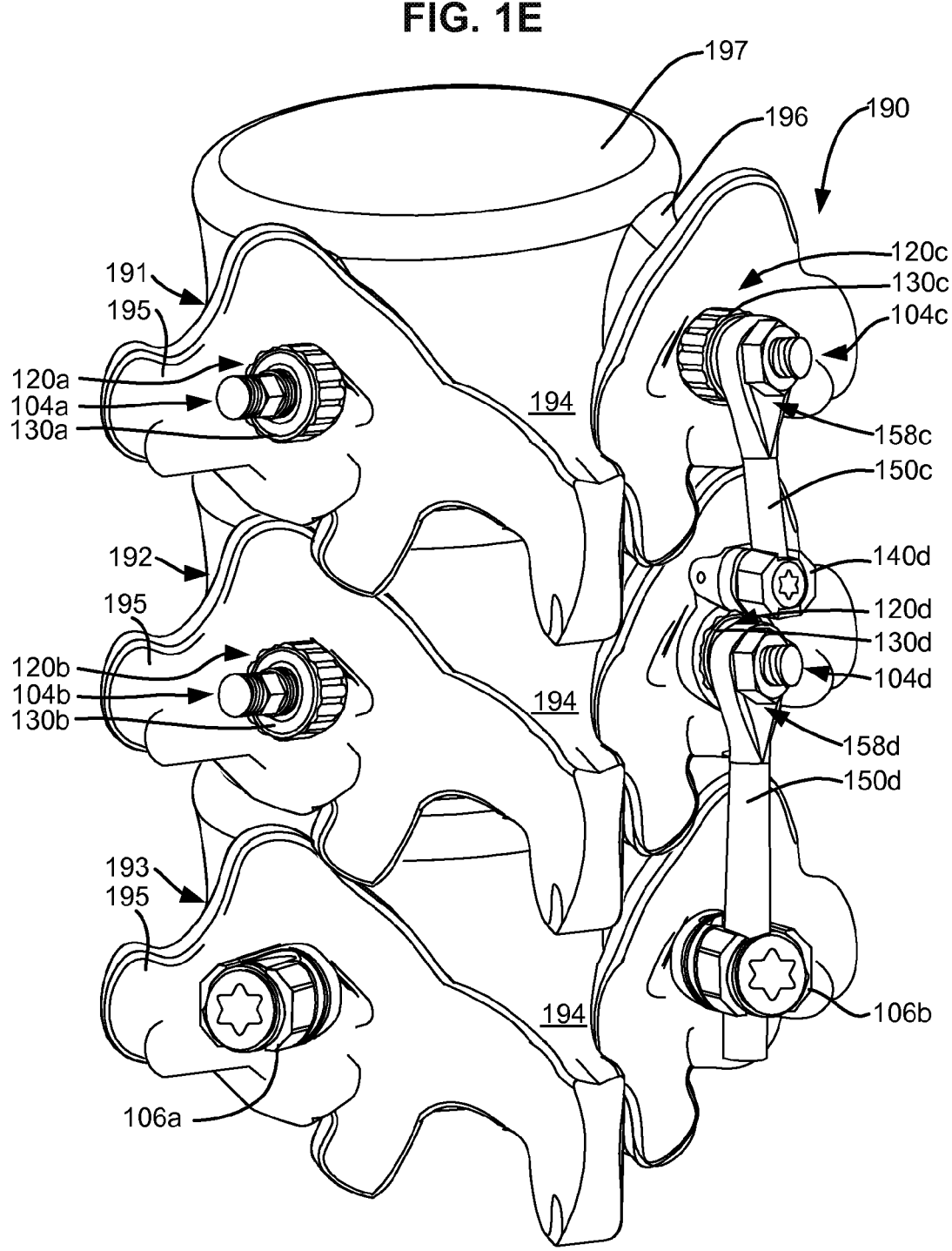

FIG. 2A
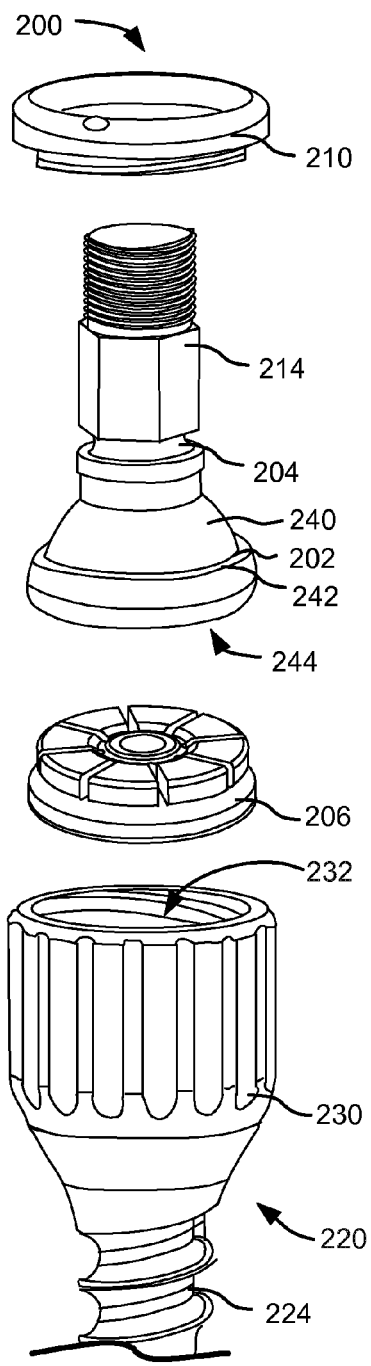
FIG. 2B
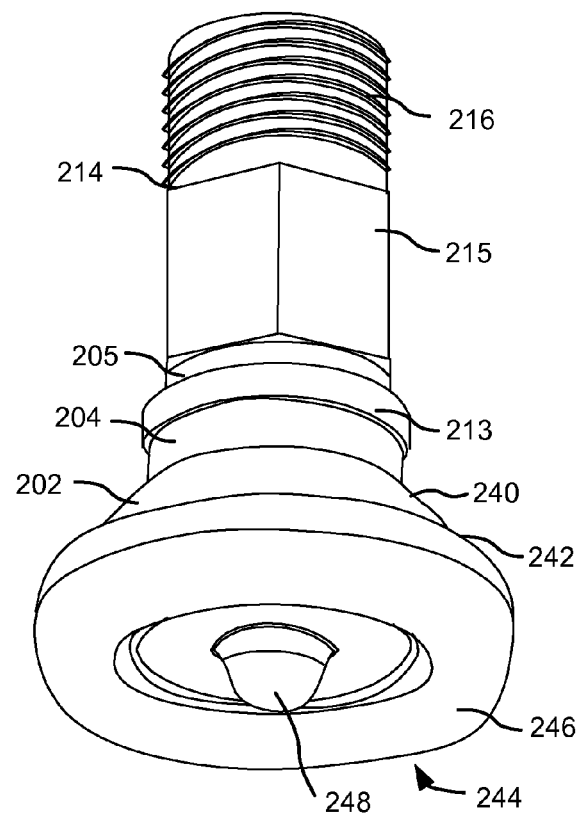
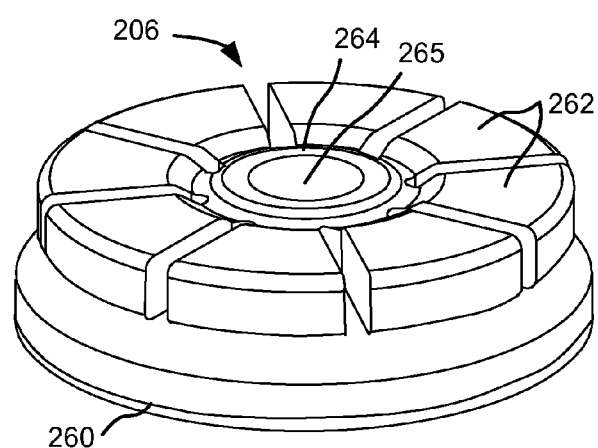
FIG. 2C

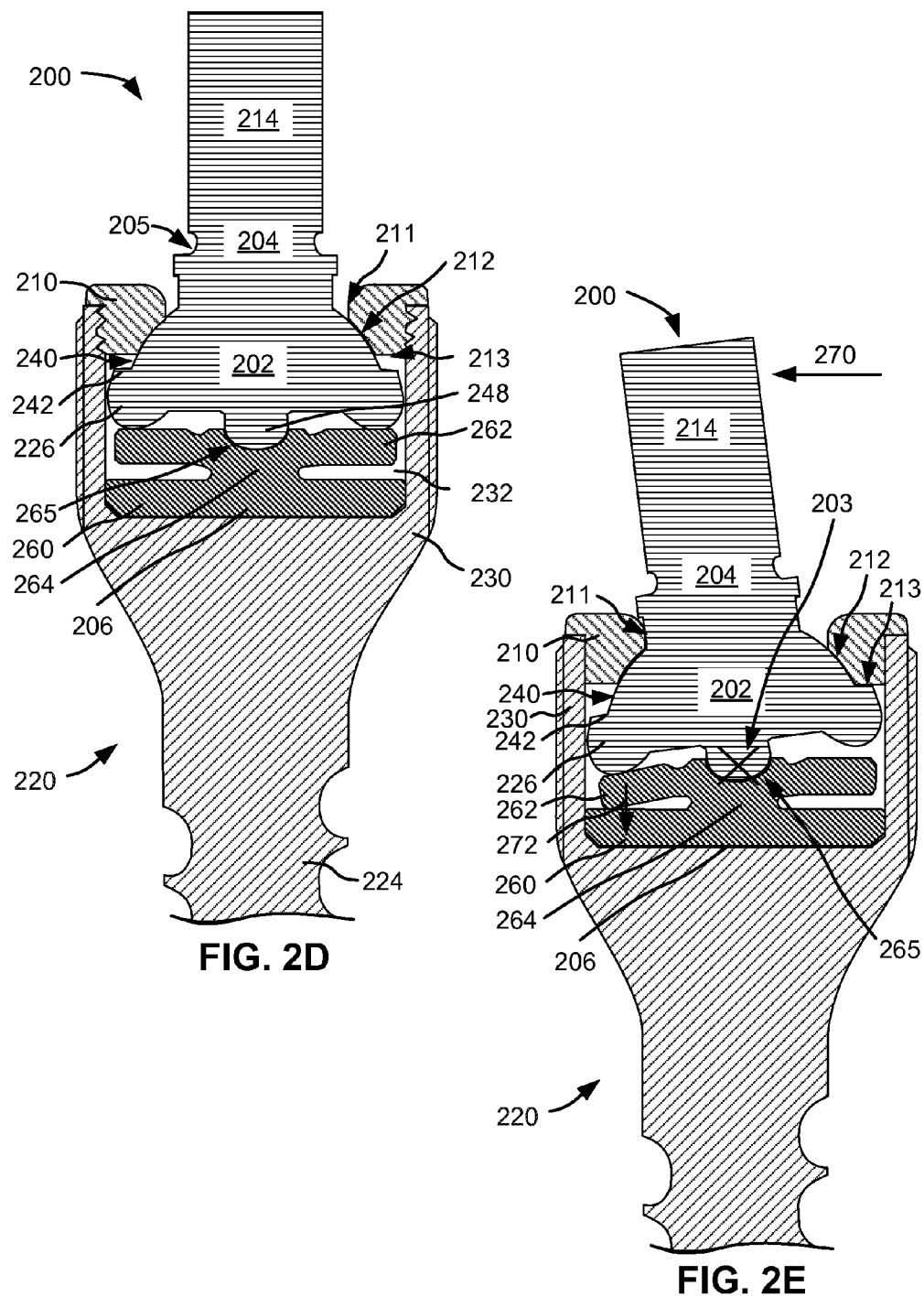

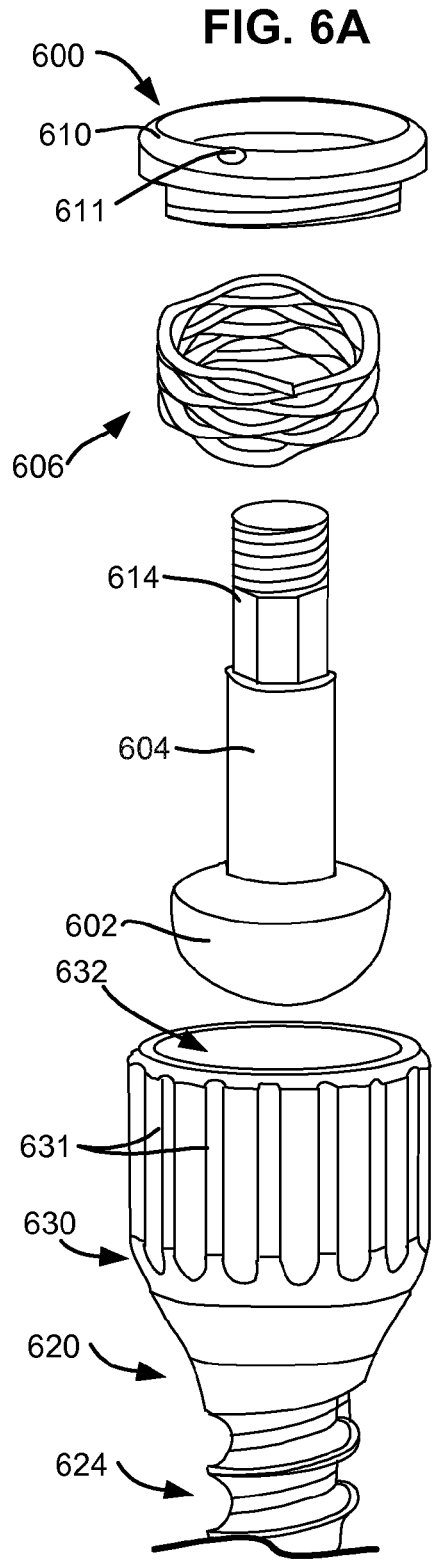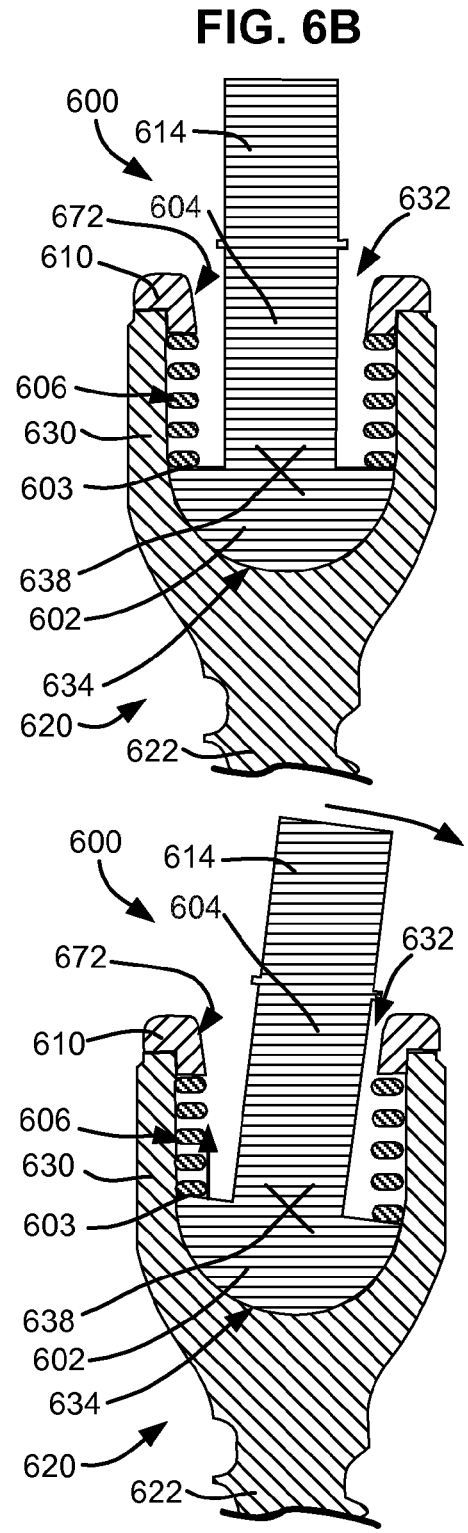

LOAD-SHARING BONE ANCHOR HAVING A DEFLECTABLE POST AND AXIAL SPRING AND METHOD FOR DYNAMIC STABILIZATION OF THE SPINE

CLAIM TO PRIORITY

This application claims priority to the following patents and patent applications:

U.S. Provisional Application No. 61/100,593 filed Sep. 26, 2008, entitled "A Spine Implant With A Deflection Rod System Selectively Alignable And Selectively Lockable To A Bone Anchor And Method"; and U.S. Provisional Application No. 61/100,625 filed Sep. 26, 2008, entitled "Versatile Components And Methods For Dynamic Stabilization"; and U.S. Provisional Application No. 61/119,651 filed Dec. 3, 2008, entitled "Load-sharing Component Having A Deflectable Post And Methods For Dynamic Spinal Stabilization"; and U.S. Provisional Application No. 61/122,658 filed Dec. 15, 2008, entitled "Load-sharing Component Having A Deflectable Post And Methods For Dynamic Spinal Stabilization"; and U.S. Provisional Application No. 61/144,426 filed Jan. 13, 2009, entitled "Load-sharing Component Having A Deflectable Post And Methods For Dynamic Spinal Stabilization"; and U.S. Provisional Application No. 61/225,478 filed Jul. 14, 2009, entitled "Load-sharing Component Having A Deflectable Post And Methods For Dynamic Spinal Stabilization"; and U.S. Provisional Application No. 61/167,789 filed Apr. 8, 2009, entitled "Load-sharing Component Having A Deflectable Post And Spring And Methods For Dynamic Spinal Stabilization"; and U.S. Provisional Application No. 61/217,556 filed Jun. 1, 2009, entitled "Load-sharing Component Having A Deflectable Post And Axially-Compressible Spring And Methods For Dynamic Spinal Stabilization".

The present application is a continuation-in-part of U.S. patent application Ser. No. 12/130,395, filed May 30, 2008 now U.S. Pat. No. 8,070,775, entitled "A Deflection Rod System For A Dynamic Stabilization And Motion Preservation Spinal Implantation System And Method" which claims priority to U.S. Provisional Application No. 61/031,598 filed Feb. 26, 2008 and entitled "A Deflection Rod System For A Dynamic Stabilization And Motion Preservation Spinal Implantation System And Method".

The present application is also a continuation-in-part of U.S. patent application Ser. No. 12/130,095, filed May 30, 2008, entitled "A Spine Implant With A Deflection Rod System Including A Deflection Limiting Shield Associated With A Bone Screw And Method" which claims priority to U.S. Provisional Application No. 61/057,340 filed May 30, 2008, entitled "A Spine Implant With A Deflection Rod System Aligned With A Bone Anchor And Method".

All of the afore-mentioned patent applications are incorporated herein by reference in their entireties.

CROSS-REFERENCES TO RELATED APPLICATIONS

This application is related to all of the afore-mentioned patent applications. This application is also related to all of the following applications including:

U.S. patent application Ser. No. 12/566,478, filed Sep. 24, 2009, entitled "A Modular In-Line Deflection Rod And Bone Anchor System And Method For Dynamic Stabilization Of The Spine"; and U.S. patent application Ser. No. 12/566,485, filed Sep. 24, 2009, entitled "Versatile Polyaxial Connector Assembly And Method For Dynamic Stabilization Of The Spine"; and U.S. patent application Ser. No. 12/566,487, filed Sep. 24, 2009, entitled "Versatile Offset Polyaxial Connector And Method For Dynamic Stabilization Of The Spine"; and U.S. patent application Ser. No. 12/566,491, filed Sep. 24, 2009, entitled "Load-Sharing Bone Anchor Having A Deflectable Post and Method For Dynamic Stabilization Of The Spine"; and U.S. patent application ser. No. 12/566,494, filed Sep. 24, 2009, entitled "Load-Sharing Component Having A Deflectable Post And Method For Dynamic Stabilization Of The Spine"; and U.S. patent application Ser. No. 12/566,498, filed Sep. 24, 2009, entitled "Load-Sharing Bone Anchor Having A Durable Compliant Member And Method For Dynamic Stabilization Of The Spine"; and U.S. patent application Ser. No. 12/566,504, filed Sep. 24, 2009, entitled "Load-Sharing Bone Anchor Having A Deflectable Post With A Compliant Ring And Method For Stabilization Of The Spine"; and U.S. patent application Ser. No. 12/566,507, filed Sep. 24, 2009, entitled "Load-Sharing Bone Anchor Having A Deflectable Post With A Compliant Ring And Method For Stabilization Of The Spine"; and U.S. patent application Ser. No. 12/566,511, filed Sep. 24, 2009, entitled "Load-Sharing Bone Anchor Having A Deflectable Post And Method For Stabilization Of The Spine"; and U.S. patent application Ser. No. 12/566,516, filed Sep. 24, 2009, entitled "Load-Sharing Bone Anchor Having A Deflectable Post And Method For Stabilization Of The Spine"; and U.S. patent application Ser. No. 12/566,519, filed Sep. 24, 2009, entitled "Dynamic Spinal Rod And Method For Dynamic Stabilization Of The Spine"; and U.S. patent application Ser. No. 12/566,522, filed Sep. 24, 2009, entitled "Dynamic Spinal Rod Assembly And Method For Dynamic Stabilization Of The Spine"; and U.S. patent application Ser. No. 12/566,529, filed Sep. 24, 2009, entitled "Configurable Dynamic Spinal Rod And Method For Dynamic Stabilization Of The Spine"; and U.S. patent application Ser. No. 12/566,531, filed Sep. 24, 2009, entitled "A Spinal Prosthesis Having A Three Bar Linkage For Motion Preservation And Dynamic Stabilization Of The Spine"; and U.S. patent application ser. No. 12/566,534, filed Sep. 24, 2009, entitled "Surgical Tool And Method For Implantation of A Dynamic Bone Anchor"; and U.S. patent application Ser. No. 12/566,547, filed Sep. 24, 2009, entitled "Surgical Tool And Method For Connecting A Dynamic Bone Anchor and Dynamic Vertical Rod"; and U.S. patent application Ser. No. 12/566,551, filed Sep. 24, 2009, entitled "Load-Sharing Bone Anchor Having A Deflectable Post And Centering Spring And Method For Dynamic Stabilization Of The Spine"; and U.S. patent application Ser. No. 12/566,553, filed Sep. 24, 2009, entitled "Load-Sharing Component Having A Deflectable Post And Centering Spring And Method For Dynamic Stabilization Of The Spine"; and U.S. patent application Ser. No. 12/566,559, filed Sep. 24, 2009, entitled "Load-Sharing Bone Anchor Having A Deflectable Post And Axial Spring And Method For Dynamic Stabilization Of The Spine".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages, e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by providing and implanting a dynamic spinal stabilization assembly which supports the spine while preserving motion. These and other objects, features and advantages of the invention will be apparent from the drawings and detailed description which follow.

BRIEF DESCRIPTION OF THE DRAWINGS

FIG. 1A is a perspective view of a deflection rod assembled with a bone anchor according to an embodiment of the present invention.

FIG. 1B is a perspective view of an offset connector mounted to the bone anchor of FIG. 1A.

FIG. 1C is an exploded view of a dynamic rod according to an embodiment of the present invention.

FIG. 1D is a perspective view of the dynamic rod of FIG. 1C mounted to the bone anchor of FIG. 1A.

FIG. 1E is a posterior view of a multi-level dynamic stabilization assembly utilizing the components of FIGS. 1A to 1D according to an embodiment of the present invention.

FIG. 2A is an exploded view of a deflection rod according to an embodiment of the present invention.

FIG. 2B is an enlarged view of the deflectable rod, mount and retainer of FIG. 2A FIG. 2C is a perspective view of the spring of FIG. 2A.

FIGS. 2D and 2E are sectional views of the deflection rod of FIG. 2A.

FIG. 6A is an exploded view of an alternative deflection rod according to an embodiment of the present invention.

FIGS. 6B and 6C are sectional views of the deflection rod of FIG. 6A.

DETAILED DESCRIPTION OF THE PREFERRED EMBODIMENTS

Figure 1F:
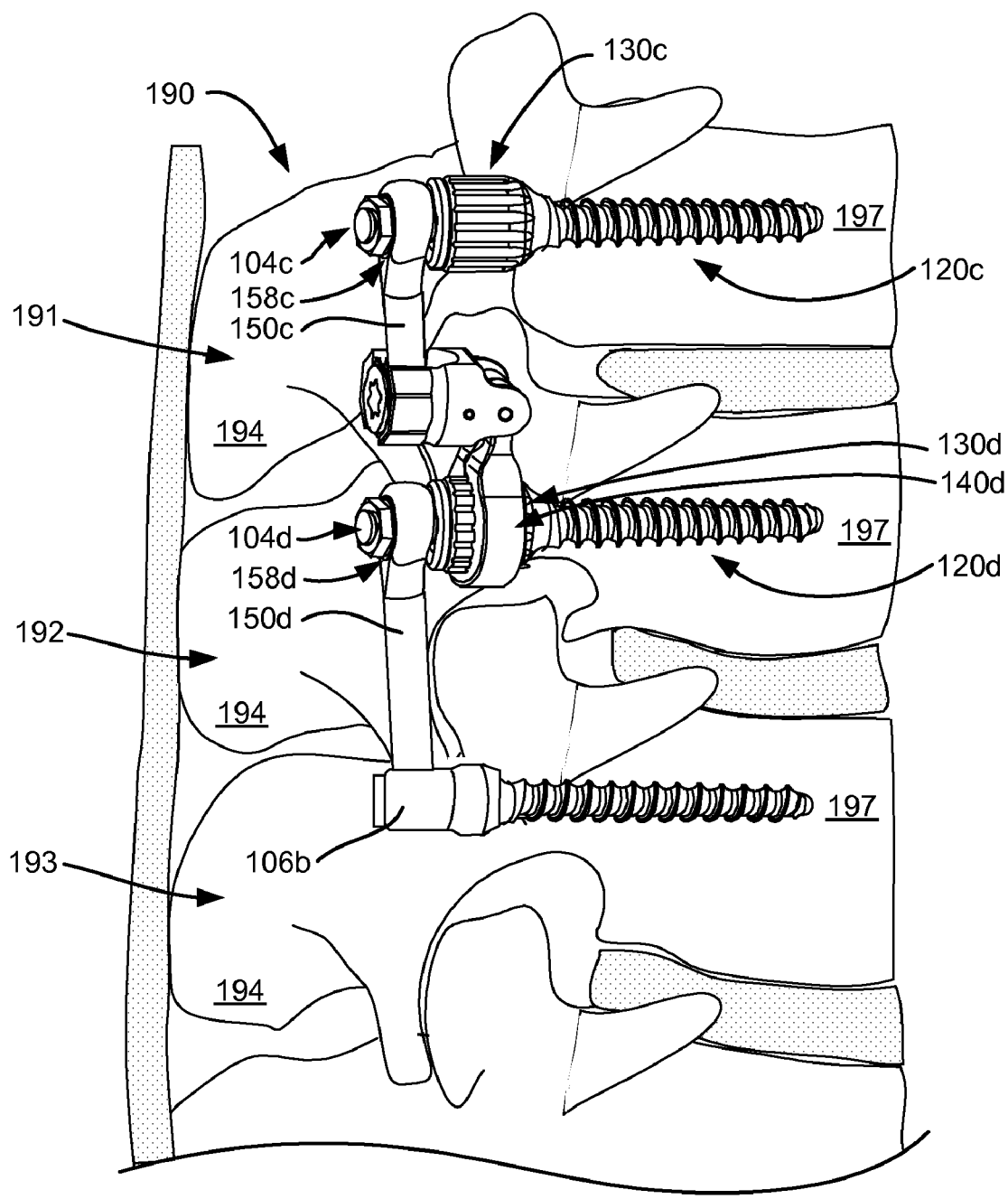
FIG. 1F is a lateral view of a multi-level dynamic stabilization assembly utilizing the components of FIGS. 1A to 1D according to an embodiment of the present invention.

The present invention includes a versatile spinal implant system and methods which can dynamically stabilize the spine while providing for the preservation of spinal motion. Alternative embodiments can be used for spinal fusion. An aspect of the invention is restoring and/or preserving the natural motion of the spine including the quality of motion as well as the range of motion. Still, another aspect of the invention is providing for load sharing and stabilization of the spine while preserving motion.

Another aspect of the invention is to provide a modular system which can be customized to the needs of the patient. Another aspect of embodiments of the invention is the ability to stabilize two, three and/or more levels of the spine by the selection of appropriate components for implantation in a patient. Another aspect of the invention is the ability to provide for higher stiffness and fusion at one level or to one portion of the spine while allowing for lower stiffness and dynamic stabilization at another adjacent level or to another portion of the spine. Embodiments of the invention allow for fused levels to be placed next to dynamically-stabilized levels. Such embodiments of the invention enable vertebral levels adjacent to fusion levels to be shielded by providing a transition from a rigid fusion level to a dynamically stable, motion preserved, and more mobile level.

Embodiments of the present invention provide for assembly of a dynamic stabilization system which supports the spine while providing for the preservation of spinal motion.

The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes coaxial connectors and offset connectors which adjustably connect the deflection system, vertical rod system and anchor system allowing for appropriate, efficient and convenient placement of the anchor system relative to the spine. Alternative embodiments can be used for spinal fusion.

Embodiments of the invention include a construct with an anchor system, a deflection system, a vertical rod system and a connection system. The deflection system provides dynamic stabilization while reducing the stress exerted upon the bone anchors and spinal anatomy. The anchor system anchors the deflection system to the spine. The connection system connects the deflection system to the vertical rod system. The vertical rod system connects dynamic stabilization system components on different vertebra to provide load sharing and dynamic stabilization.

Embodiments of the present invention include a deflection rod which provides load sharing while preserving range of motion and reducing stress exerted upon the bone anchors and spinal anatomy. The deflection rod includes a deflectable post mounted within a bone anchor. Deflection of the deflectable post is controlled by a spring. Deflection of the deflectable post results in compression of the spring in an axial direction relative to the bone anchor—i.e. in a direction parallel to the longitudinal axis of the bone anchor. A contact surface of the deflection rod is positioned to limit deflection of the deflectable post. The force-deflection properties of the deflection rod may be adapted and/or customized to the anatomy and functional requirements of the patient by changing the properties of the spring. Different deflection rods having different force-deflection properties may be utilized in different patients or at different spinal levels within the same patient depending upon the anatomy and functional requirements.

Common reference numerals are used to indicate like elements throughout the drawings and detailed description; therefore, reference numerals used in a drawing may or may not be referenced in the detailed description specific to such drawing if the associated element is described elsewhere. The first digit in a reference numeral indicates the series of figures in which the referenced item first appears.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a screw that enters a bone would conventionally be called the distal end (it is furthest from the surgeon) while the head of the screw would be termed the proximal end (it is closest to the surgeon).

Dynamic Stabilization System

FIGS. 1A-1F introduce components of a dynamic stabilization system according to an embodiment of the present invention. The components include anchor system components, deflection rods, vertical rods and connection system components, including for example coaxial and offset connectors. The components may be implanted and assembled to form a dynamic stabilization system appropriate for the anatomical and functional needs of a patient.

FIG. 1A shows a bone anchor 120 and a deflection rod 104. Deflection rod 104 is an example of a component of the deflection system. Deflection rod 104 is a component having controlled flexibility which allows for load sharing. The deflection rod 104 provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod in order to match the load sharing characteristics desired. For embodiments of this invention, the terms "deflection rod" and "loading rod" can be used interchangeably. Deflection rods, deflection rod mountings and alternative deflection rods are described in more detail below.

Bone anchor 120 is an example of a component of the anchor system. Bone anchor 120 includes a housing 130 at the proximal end. Housing 130 has a bore 132 coaxial with the longitudinal axis of bone anchor 120. As shown in FIG. 1A, bone anchor 120 has a threaded shank 124 which engages a bone to secure the bone anchor 120 onto a bone. The anchor system may include one or more bone anchors including alternative bone anchors known in the art e.g. bone screws, bone hooks, expanding devices, barbed devices, threaded devices, sutures, staples, adhesive and other devices capable of securing a component to bone instead of or in addition to bone anchor 120. Different bone anchors may be used to anchor the system to different positions in the spine depending upon the anatomy and needs of the patient.

Deflection rod 104 includes a deflectable post 105 which may deflect relative to a bone anchor 120. Deflectable post 105 may deflect in a controlled manner relative to bone anchor 120 thereby provide for load sharing while preserving range of motion of the patient. The stiffness/flexibility of deflection of the deflectable post 105 relative to the bone anchor 120 may be controlled and/or customized as will be described below.

A collar 110 is adapted to secure the deflectable post 105 within cavity 132 of bone anchor 120. Collar 110 is secured into a fixed position relative to bone anchor 120 by threads and or a welded joint. As shown in FIG. 1A, bone anchor 120 includes a housing 130 at the proximal end. Housing 130 includes a cavity 132 for receiving deflection rod 104. Cavity 132 is coaxial with threaded bone anchor 120. The proximal end of cavity 132 is threaded (not shown) to receive and engage collar 110. Alternative mechanisms and techniques may be used to secure the deflection rod to the bone anchor including for example, welding, soldering, bonding, and/or mechanical fittings including threads, snap-rings, locking washers, cotter pins, bayonet fittings or other mechanical joints.

As shown in FIG. 1A, deflection rod 104 and deflectable post 105 are oriented in a co-axial, collinear or parallel orientation to bone anchor 120. This arrangement simplifies implantation, reduces trauma to structures surrounding an implantation site, and reduces system complexity. Arranging the deflection rod co-axial with the bone anchor 120 can substantially transfer a moment (of) force applied by the deflectable post 105 from a moment force tending to pivot or rotate the bone anchor 120 about the axis of the shaft, to a moment force tending to act perpendicular to the axis of the shaft. The deflection rod can thereby effectively resist repositioning of the deflection rod and/or bone anchor 120 without the use of locking screws or horizontal bars to resist rotation.

Moreover, because deflectable post 105 may undergo controlled deflection in response to loads exerted upon it be the vertical rod system, the deflectable post isolates the bone anchor 120 from many loads and motions present in the vertical rod system. Further examples of coaxial deflection rods are provided below. Each of the deflection rods described herein may be used as a component of a dynamic stabilization system.

Bone anchor 120 also includes a coupling 136 to which other components may be mounted. As shown in FIG. 1A, coupling 136 is the external cylindrical surface of housing 130. Housing 130 thus provides two mounting positions, one being the mount 114 of deflectable post 105 (a coaxial mounting position) and one being the surface of housing 130 (an external or offset mounting position). Thus, a single bone anchor 120 can serve as the mounting point for one, two or more components. A deflection rod 104 may be coaxially mounted in the cavity 132 of the housing 130 and one or more additional components may be externally mounted to the outer surface of the housing—coupling 136. For example, a component of the connection system may be mounted to the outer surface 136 of the housing—such a connector may be called an offset head or offset connector (See, e.g. FIG. 1B). In alternative embodiments, a component of the connection system may be coaxially-mounted in the cavity 132 in place of a deflection rod 104—such a connector may be called a coaxial head or coaxial connector.

FIG. 1B shows a component of the connection system which may be mounted externally to the housing 130 of bone anchor 120 in conjunction with a coaxially-mounted component. FIG. 1B shows a perspective view of offset connector 140 mounted externally to housing 130 of bone anchor 120 in which a deflection rod 104 is coaxially mounted. Connector 140 may be termed an offset head or offset connector. Offset connector 140 comprises six components and allows for two degrees of freedom of orientation and two degrees of freedom of position in connecting a vertical rod to a bone anchor. The six components of offset connector 140 are dowel pin 142, pivot pin 144, locking set screw 146, plunger 148, clamp ring 141 and saddle 143. Saddle 143 has a slot 184 sized to receive a rod which may be a vertical rod e.g. vertical rod 106 of FIG. 1A. Locking set screw 146 is mounted at one end of slot 184 such that it may be tightened to secure a rod within slot 184.

Clamp ring 141 is sized such that, when relaxed it can slide freely up and down the housing 130 of bone anchor 120 and rotate around the housing 130. However, when locking set screw 146 is tightened on a rod, the clamp ring 141 grips the housing and prevents the offset connector 140 from moving in any direction. Saddle 143 is pivotably connected to clamp ring 141 by pivot pin 144. Saddle 143 can pivot about pivot pin 144. However, when locking set screw 146 is tightened on a rod, the plunger 148 grips the clamp ring 141 and prevents further movement of the saddle 143. In this way, operation of the single set screw 146 serves to lock the clamp ring 141 to the housing 130 of the bone anchor 120, fix saddle 143 in a fixed position relative to clamp ring 141 and secure a rod within the slot 184 of offset connector 140.

The connector of FIG. 1B is provided by way of example only. It is desirable to have a range of different connectors which are compatible with the anchor system and deflection system. The connectors may have different attributes including, for example, different degrees of freedom, range of motion, and amount of offset which attributes may be more or less appropriate for a particular relative orientation and position of two bone anchors and/or patient anatomy. It is desirable that each connector be sufficiently versatile to connect a vertical rod to a bone anchor in a range of positions and orientations while being simple for the surgeon to adjust and secure. It is desirable to provide a set of connectors which allows the dynamic stabilization system to be assembled in a manner that adapts a particular dynamic stabilization assembly to the patient anatomy rather than adapting the patient anatomy for implantation of the assembly (for example by removing tissue\bone to accommodate the system). In a preferred embodiment, the set of connectors comprising the connection system have sufficient flexibility to allow the dynamic stabilization system to realize a suitable dynamic stabilization assembly in all situations that will be encountered within the defined patient population. Alternative embodiments of coaxial heads and offset connectors can be found in the related patent applications incorporated by reference above.

A vertical rod component may also be mounted to mount 114 of deflectable post 105. FIG. 1C shows an exploded view of a vertical rod 150. Vertical rod 150 includes an elongated rod 156 which is preferably a 5 mm titanium rod. At one end of rod 156 is a pocket 157. Pocket 157 is shaped to receive a chrome ball 152. Ball 152 has a central aperture 153 shaped to receive mount 114 of deflection rod 104. Aperture 153 passes through the center of ball 152 and may be cylindrical or may be polygonal in section. Ball 152 is received in pocket 157 and then secured in place by cap 154. Cap 154 and pocket 157 may be threaded in order that cap 154 may be secured to rod 156. Cap 154 may also be secured to rod 156 by laser welding or other bonding technology. After being secured in pocket 157 by cap 154, ball 152 is still free to rotate within pocket 157. FIG. 1D shows vertical rod 150 mounted to a mount 114 of a deflectable post 105. As shown in FIG. 1D, mount 114 is passed through aperture 153 of ball 152 (not shown). A nut 160 is then secured to mount 114 securing ball 152 to mount 114. Nut 160 secures ball 152 to mount 114. However, vertical rod 150 may still rotate around ball 152 and pivot relative to deflectable post 105. Note that a connector 140, such as shown in FIG. 1B, may be mounted to housing 130 to connect bone anchor 120 to a second vertical rod (not shown).

The components of the dynamic stabilization system may be assembled and implanted in the spine of a patient to provide a multilevel dynamic stabilization assembly which provides dynamic stabilization of the spine and load sharing. In some embodiments the bone anchors may be implanted with the deflection rod/connection component already installed and/or built in. FIGS. 1E and 1F, shows posterior and lateral views of three adjacent vertebrae 191, 192 and 193. Referring first to FIG. 1E, as a preliminary step, bone anchors 120a, 120b, 120c, and 120d comprising deflection rods 104a, 104b, 104c and 104d have been implanted in vertebrae 191 and 192 on the left and right sides of the spinous process 194 between the spinous process 194 and the transverse process 195 in the pedicles 196 of each vertebra. In the example shown in FIG. 1E, polyaxial screws 106a, 106b are implanted in the pedicles 196 of vertebra 193.

In preferred procedures, the bone anchor is directed so that the threaded portion is implanted within one of the pedicles 196 angled towards the vertebral body 197 of each vertebra. The threaded region of each bone anchor is fully implanted in the vertebrae 191, 192. As shown in FIG. 1F, the bone anchors 120a, 102b, 120c are long enough that the threaded portion of the bone anchor extends into the vertebral body 197 of the vertebra. As shown in FIG. 1E, the housings 130a, 130b, 130c, 130d of each bone anchor remain partly or completely exposed above the surface of the vertebrae so a connection system component can be secured to each bone anchor 120a, 120b, 120c and 120d. In order to implant the bone anchors, a driver is used to engage the housing 130a, 130b, 130c, 130d of each bone anchor in order to drive the threaded portion of each bone anchor into the bone. The driver may have a torque-measuring and/or torque limiting function to assist in accurate implantation of the bone anchor and avoid excess force being applied to the vertebrae. In alternative embodiments, the bone anchor may incorporate a torque limiting element, for example a secondary head which breaks away when the driver torque exceeds a predetermined torque limit.

After installation of bone anchors 120a, 120b, 120c, 120d and polyaxial screws 106a, 106b, the vertical rod system components and connection system components may be installed and assembled. FIG. 1E shows, on the right side of the vertebrae, one way to assemble deflection system components and connection system components. (See also, lateral view of FIG. 1F). Offset heads/connectors may be externally-mounted to the outside surface of each of housings 130a, 130b, 130c and 130d. An offset connector 140d is shown mounted to housing 130d or bone anchor 120d. A first vertical rod 106a is connected at one end to deflection rod 104c by ball joint 108c. Vertical rod 106a is connected at the other end by offset connector 140d to bone anchor 120d. A second vertical rod 106b is connected at one end to deflection rod 104d by ball joint 108d. Vertical rod 106b is connected at the other end to polyaxial screw 106b.

The dynamic stabilization assembly 190 of FIG. 1E thus has a vertical rod 106a, 106b stabilizing each spinal level (191-192 and 192-193). Each of the vertical rods 106a, 106b is secured rigidly at one end to a bone anchor (120b, 120c). Each of the vertical rods 106a, 106b is secured at the other end by a ball joint to a deflection rod 104c, 104d thereby allowing for some movement and load sharing by the dynamic stabilization assembly. Offset connector 140d permits assembly of the dynamic stabilization assembly for a wide range of different patient anatomies and/or placements of bone anchors 120a, 120b, 120c and 120d. An identical or similar dynamic stabilization assembly would preferably be implanted on the left side of the spine (See FIG. 1E).

It should be noted that the dynamic stabilization assembly of the present invention does not require horizontal bars or locking screws thereby reducing the exposure of tissue and/or bone to foreign bodies compared to systems with this additional hardware. The dynamic stabilization assembly thereby, has a small footprint, potentially reducing the amount of displacement of tissue and/or bone, reducing trauma to tissue and/or bone during surgery. Further, the smaller footprint can reduce the amount of tissue that needs to be exposed during implantation.

The dynamic stabilization assembly and components shown in FIGS. 1A-1F are provided by way of example only. It is an aspect of preferred embodiments of the present invention that a range of components be provided and that the components may be assembled in different combinations and organizations to create different assemblies suitable for the functional needs and anatomy of different patients. Likewise deflection rod having different force deflection characteristics may be incorporated at different levels in accordance with the anatomical and functional requirements. Dynamic stabilization may be provided at one or more motion segments and in some cases dynamic stabilization may be provided at one or more motion segments in conjunction with fusion at an adjacent motion segment. Particular dynamic stabilization assemblies may incorporate various combinations of the bone anchors, vertical rods, deflection rods, offset and coaxial connectors described herein and in the related applications incorporated by reference as well as standard spinal stabilization and/or fusion components, for example screws, rods and polyaxial screws.

Deflection Rods/Loading Rods

One feature of embodiments of the present invention is the load sharing and range of motion provided by the deflection system and deflection rods of the deflection system. The deflection rod provides stiffness and support where needed to support the loads exerted on the spine during normal spine motion thereby recovering improved spine function without sacrificing all motion. The deflection rod also isolates the anchor system components from forces exerted by the dynamic stabilization assembly thereby reducing stress on the bone anchors and the bone to which they are attached. Moreover, by selecting the appropriate stiffness of the deflection rod to match the physiology of the patient and the loads that the patient places on the spine, a better outcome is realized for the patient.

Deflection rods of the present invention provide load sharing while preserving range of motion and reducing stress exerted upon the bone anchors and spinal anatomy. The deflection rods include a deflectable post mounted within a bone anchor. Deflection of the deflectable post is controlled by a spring. Deflection of the deflectable post results in compression of the spring in an axial direction relative to the bone anchor—i.e. in a direction parallel to the longitudinal axis of the bone anchor. The force-deflection properties of the deflection rod may be adapted and/or customized to the anatomy and functional requirements of the patient by changing the properties of the spring. Different deflection rods having different force-deflection properties may be utilized in different patients or at different spinal levels within the same patient depending upon the anatomy and functional requirements.

The deflection rod includes a deflectable post, a spring and a mounting/securing device. The deflectable post and mounting/securing device are typically made of biocompatible metal or metals, e.g. titanium and stainless steel. The spring may include biocompatible metals as well as biocompatible polymers. Suitable polymers include, for example, PEEK and Bionate®. Suitable metals include, for example, titanium, steel and Nitinol. The mounting/securing device secures the deflection rod to an anchoring device, for example a bone anchor. The mounting securing device has a proximal housing which receives the deflectable post. The housing has a cavity which is coaxial with the mounting/securing device. The deflectable post and spring are received in the coaxial cavity in a manner which allows deflection of the deflectable post under the control of the spring. The deflectable post is generally held substantially coaxial or collinear with the bone anchor.

The deflectable post has a free end configured to connect to the vertical rod system. The free end of the deflectable post protrudes from the housing of the bone anchor. The free end of the deflectable post has a mounting to facilitate connecting it to a vertical rod system. The mounting may be for example a threaded post or a ball. The deflectable post may deflect relative to the anchoring device by compressing the spring. The movement of the deflectable post relative to the anchoring device allows controlled movement of the bone anchor (and vertebra in which it is implanted) relative to the vertical rod system. The deflection rod thus supports the vertebrae to which the bone anchors are attached while allowing movement of the vertebrae thereby providing for dynamic stabilization of the spine. In a dynamic stabilization assembly incorporating the deflection rod, the load sharing and deflection is provided by the deflection rod and to a lesser degree or not in the vertical rod.

Deflection of the deflectable post deforms the spring of the deflection rod. The deformation of the spring imparts force-deflection characteristics to the deflectable post. Deflection rods can be manufactured in a range from stiff configurations to compliant configurations by appropriate selection of the design, materials and dimensions of the post, spring and shield/housing. In particular the spring rate of the spring can be adjusted to control the stiffness/flexibility of the deflection rod. Deflection rods having a particular stiffness/flexibility may be selected for use in a dynamic stabilization assembly based upon the physiological needs of a particular patient. In a preferred embodiment deflection rod stiffness/flexibility is selected so as to provide load sharing in conjunction with from 50% to 100% of the normal range of motion of a patient and more preferably 70% to 100% of the normal range of motion of a patient.

In some cases, certain of the deflection rods of a dynamic stabilization assembly can have a different stiffness or compliance than other of the deflection rods. Thus, in the same assembly, a first deflection rod can have a first flexibility or stiffness or rigidity, and a second deflection rod can have a second different flexibility or stiffness or rigidity depending on the needs of the patient. Particular embodiments of a dynamic stabilization assembly may utilize deflection rods having different deflection properties for each level and/or side of the dynamic stabilization assembly. In other words, one portion of a dynamic stabilization assembly may offer more resistance to movement than the other portion based on the design and selection of different on the deflection rods having different stiffness characteristics, if that configuration benefits the patient.

FIGS. 2A through 2E illustrate the design and operation of a first embodiment of a deflection rod according to the present invention. FIG. 2A shows an exploded view of deflection rod 200. Deflection rod 200 includes retainer 202, deflectable post 204, spring 206, collar 210, and mount 214. Deflection rod 200 is assembled with a bone anchor 220. Bone anchor 220 includes a threaded bone anchor 224 having a housing 230 at the proximal end. Housing 230 contains a cavity 232 which is coaxial with bone anchor 224. Deflection rod 200 is assembled within cavity 232 such that deflectable post 204 is generally coaxial or collinear with the longitudinal axis of bone anchor 224 when not loaded. The deflectable post 204 is configured so that deflection of the deflectable post 204 causes compression of spring 206 in a direction generally parallel to the axis of bone anchor 220. (See, e.g. FIGS. 2D & 2E).

FIG. 2B shows an enlarged perspective view of deflectable post 204, retainer 202 and mount 214, which are made in one piece in this embodiment. Mount 214 is formed at the proximal end of deflectable post 204 and includes a lip 213, hexagonal portion 215 and threaded portion 216. Mount 214 is configured for attachment of a vertical rod which may be secured in place over hexagonal portion 215 against lip 213 by a nut (not shown) secured to threaded portion 216. A groove 205 is provided between lip 213 and hexagonal portion 215 as strain relief.

Referring again to FIG. 2B, retainer 202 is formed at the distal end of deflectable post 204. Retainer 202 has a curved proximal surface 240 which is generally hemispherical. Deflectable post 204 extends from the center of curved proximal surface 240. At the edge of curved proximal surface 240 is a lip 242. The distal surface 244 is generally planar and oriented perpendicular to the longitudinal axis of deflectable post 204. The distal surface has a peripheral ridge 246 adjacent the periphery for deflecting the spring 206. The distal surface also has a central nub 248 which forms the pivot point about which deflectable post 204 may deflect. In alternative embodiments retainer 202 and/or mount 214 may be formed separately from deflectable post 204 and attached to deflectable post 204 by laser welding, soldering or other bonding technology. Alternatively, retainer 202 and/or mount 214 may mechanically engage the deflectable post 204 using, for example, threads.

FIG. 2C shows an enlarged perspective view of spring 206. As shown in FIG. 2B, spring 206 comprises a circular base 260. From the middle of circular base 260 protrudes a column 264 having a curved indentation 265 at the proximal end for receiving nub 248 of deflectable post 204. Extending laterally from column 264 is a plurality of lever arms 262. The material of spring 206 is selected such that the lever arms resist bending away from the position shown. Circular base 260 is designed to mate to the distal end of cavity 232 to secure spring 206 in position with lever arms 262 held perpendicular to the longitudinal axis of bone anchor 224 in the unloaded state.

The stiffness of deflection rod 200 is affected by the spring rate of spring 206. The stiffness of the deflection rod 200 can be changed for example by increasing the spring rate of lever arms 262 of spring 206 and conversely the stiffness may be reduced by decreasing the spring rate of spring 206. The spring rate of the lever arms 262 of spring 206 can be, for example, increased by increasing the thickness of the lever arms 262 and/or decreasing the length of the lever arms 262. Alternatively and/or additionally changing the materials of the spring 206 can also affect the spring rate. For example, making spring 206 out of stiffer material increases the spring rate and thus reduces deflection of deflectable post 204 for the same amount of load—all other factors being equal. Spring 206 is preferably made of a biocompatible polymer or metal. Spring 206 may, for example, be made from PEEK, Bionate®, Nitinol, steel and/or titanium.

Spring 206 may have the same spring rate in each direction of deflection of the deflectable post (isotropic). The spring 206 may have different spring rates in different directions of deflection of the deflectable post (anisotropic). For example, the spring 206 can be designed to have different spring rate in different directions by adjusting, for example, the length, thickness and/or material of the lever arms 262 in one direction compared to another direction. A deflection rod 200 incorporating an anisotropic spring would have different force-deflection characteristics imparted to it by the spring 206 in different directions.

The stiffness of the deflection rod 200 is also affected by factors beyond the spring rate of spring 206. By changing the dimensions and or geometry of the deflectable post 204, spring 206 and the shield 208, the deflection characteristics of the deflection rod 200 can be changed. For example, the stiffness of the deflection rod 200 can be increased by increasing the distance from the pivot point of the deflectable post 204 to the point of contact between the lever arms 262 surrounding aperture 264 and the deflectable post 204. Conversely, the stiffness of the deflection rod 200 can be decreased by decreasing the distance from the pivot point of the deflectable post 204 to the point of contact between the lever arms 262 surrounding aperture 264 and the deflectable post 204.

The stiffness of the deflection rod may thus be varied or customized according to the needs of a patient by controlling the material and design of spring 206 and defection rod 200. The deflection characteristics of the deflection rod 200 can be configured to approach the natural dynamic motion of the spine, while giving dynamic support to the spine in that region. It is contemplated, for example, that the deflection rod can replicate a 70% range of motion and flexibility of the natural intact spine, a 50% range of motion and flexibility of the natural intact spine and a 30% range of motion and flexibility of the natural intact spine.

One feature of the present invention is to allow the efficient manufacture of a range of deflection rods having a range of different force-deflection characteristics. This can readily be accomplished by manufacturing a range of springs having different force-deflection characteristics and leaving the remainder of the components unchanged. In this way a range of deflection rods may be manufactured with a small number of unique parts. In some cases a kit is provided to a doctor having a set of deflection rods with different force-deflection characteristics from which the doctor may select the deflection rods most suitable for a particular patient. In other cases, the surgeon may select deflection rods prior to the procedure based upon pre-operative assessment.

Referring now to FIGS. 2D and 2E, which show sectional views of a fully assembled deflection rod 200. When assembled, spring 206 is positioned in the distal end of cavity 232 of housing 230. Retainer 202 is inserted into cavity 230 so that nub 248 of retainer 202 engages indentation 265 of spring 206. Ridge 226 of retainer 202 makes contact with lever arms 262. Collar 210 is positioned over deflectable post 204 and secured into the threaded opening of cavity 232. Collar 232 has a curved surface 212 which is complementary to the curved surface 240 of retainer 202. Collar 210 secures retainer 202 within cavity 230 and traps spring 206 between retainer 202 and housing 230.

When assembled, deflectable post 204 may pivot about the center of rotation defined by spherical surface 240—marked by an "X" in FIG. 2E. Deflectable post 204 may also rotate about its longitudinal axis. FIG. 2E shows a partial sectional view of a fully assembled deflection rod 200. As shown in FIG. 2E, spring 206 occupies the space between retainer 202 and housing 230. When deflectable post 204 deflects from a position coaxial with bone anchor 220, ridge 226 pushes on spring 206 compressing spring 206. The spring 206 is compressed in a direction parallel to the axis of bone anchor 220. To put it another way a load applied transverse to the axis of the deflectable post 204 as shown by arrow 270 is absorbed by compression of spring 206 in a direction generally parallel to the axis of bone anchor 220 as shown by arrow 272.

This arrangement means that less transverse forces are transmitted to the bone anchor 220 by a load applied to deflectable post 204 until deflectable post 204 reaches the end of the range of motion and makes contact with the limit surface 211 of collar 210. Deflection rod 200 effectively isolates bone anchor 220 from these forces where the load is below a limit controlled by spring 206. The spring rate of spring 206 is selected to generate the desired deflection/load characteristics for the deflection rod. The isolation of bone anchor 220 from many transverse loads on deflectable post 204 reduces the stress placed on bone anchor 220 and the number of loading/unloading events experienced by the bone anchor/bone interface. This leads to a stronger and more durable connection between the bone anchor and the vertebra.

FIG. 2E illustrates deflection of deflectable post 204. Applying a transverse load to deflectable post 204 as shown by arrow 270 causes deflection of deflectable post 204 relative to the bone anchor to which it may be mounted. Initially deflectable post 204 pivots about a pivot point 203 indicated by an X. In this embodiment, pivot point 203 is located at the center of ball-shaped retainer 202. In other embodiments, however, pivot point 203 may be positioned at a different location. For example, for other retainer shapes disclosed in the applications incorporated by reference herein, the retainer may pivot about a point which is at the edge of the retainer or even external to the retainer. As shown in FIG. 2E, deflection of deflectable post 204 deforms the spring 206. The force required to deflect deflectable post 204 depends upon the dimensions of deflectable post 204, and spring 206 as well as the attributes of the material of spring 206. In particular, the spring rate of spring 206 and elements thereof (See FIG. 2B) may be adjusted to impart the desired force-deflection characteristics to deflectable post 204.

As shown in FIG. 2E, after further deflection, deflectable post 204 comes into contact with limit surface 211 of collar 210. Limit surface 211 is oriented such that when deflectable post 204 makes contact with limit surface 211, the contact is distributed over an area to reduce stress on deflectable post 204 and limit surface 211. Lip 242 of retainer 202 is positioned so that it makes simultaneous contact with the lower limit surface 213 of collar 210 on the opposite side of collar 210. As depicted, the limit surface 211 is configured such that as the deflectable post 204 deflects into contact with the limit surface 211, the limit surface 211 is aligned/flat relative to the deflectable post 204 in order to present a larger surface to absorb any load an also to reduce stress or damage on the deflectable.

Additional deflection of deflectable post 204 after contact with limit surface 211 may cause elastic deformation (bending) of deflectable post 204. Because deflectable post 204 is relatively stiff, the force required to deflect deflectable post 204 increases significantly after contact of deflectable post 204 with the limit surfaces 211, 213 of collar 210. For example, the stiffness may double upon contact of the deflectable post 204 with the limit surfaces 211, 213 of collar 210. In a preferred embodiment, the proximal end of deflectable post 204 may deflect from 0.5 mm to 2 mm before deflectable post 204 makes contact with limit surfaces 211, 213. More preferably deflectable post 204 may deflect approximately 1 mm before making contact with limit surfaces 211, 213.

Thus as load or force is first applied to the deflection rod by the spine, the deflection of the deflection rod responds about linearly to the increase in the load during the phase when deflection of deflectable post 204 causes compression of spring 206 as shown in FIG. 2E. After about 1 mm of deflection, when deflectable post 204 contacts limit surface 211 and lip 242 contacts lower limit surface 213 (as shown in FIG. 2E) the deflection rod becomes stiffer. Thereafter a greater amount of load or force needs to be placed on the deflection rod in order to obtain the same incremental amount of deflection that was realized prior to this point because further deflection requires bending of deflectable post 204. Accordingly, the deflection rod 200 provides a range of motion where the load supported increases about linearly as the deflection increases and then with increased deflection the load supported increases more rapidly in order to provide stabilization. To put it another way, the deflection rod 200 becomes stiffer or less compliant as the deflection/load increases.

Figure 3A:
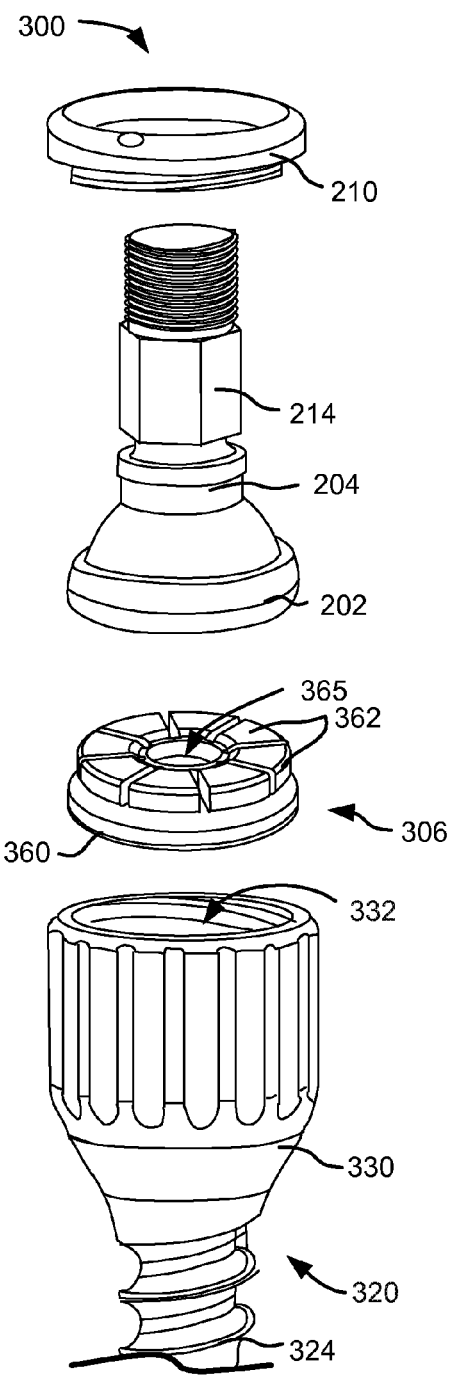
FIG. 3A is an exploded view of an alternative deflection rod according to an embodiment of the present invention.
Figure 3B:
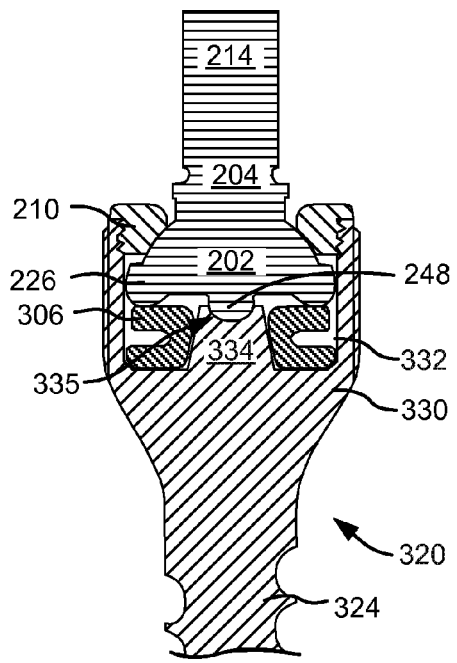
FIGS. 3B and 3C are sectional views of the deflection rod of FIG. 3A.
Figure 3C:
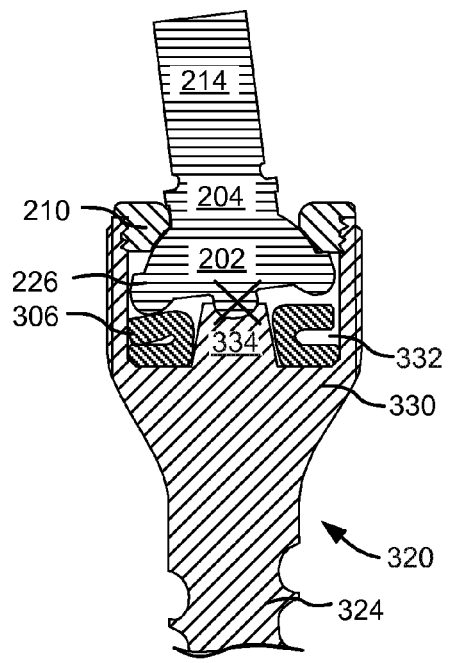

FIGS. 3A through 3C illustrate the design and operation of an alternative embodiment of a deflection rod according to an embodiment of the present invention. Deflection rod 300 is similar to deflection rod 200 of FIGS. 2A-2E. FIG. 3A shows an exploded view of deflection rod 300. FIGS. 3B and 3C show a sectional view of deflection rod 300 as assembled.

As shown in FIG. 3A, deflection rod 300 has a number of parts in common with deflection rod 200 of FIGS. 2A-2E. Deflection rod 300 includes retainer 202, deflectable post 204, spring 306, collar 210, and mount 214. Deflection rod 300 is assembled with a bone anchor 320. Bone anchor 320 includes a threaded bone anchor 324 having a housing 330 at the proximal end. Housing 330 contains a cavity 332 which is coaxial with bone anchor 224. Deflection rod 300 is assembled within cavity 332 such that deflectable post 204 is generally coaxial or collinear with the longitudinal axis of bone anchor 324 when not loaded. The deflectable post 204 is configured so that deflection of the deflectable post 204 causes compression of spring 306 in a direction generally parallel to the axis of bone anchor 320. (See, e.g. FIGS. 4A & 4B).

Spring 306 is similar in design to spring 206 with the exception that spring 306 has a central aperture 365 in place of indentation 265. Spring 306 includes a central aperture 365 which passes all the way through spring 306. As before, spring 306 has a plurality of lever arms 362. The material of spring 306 is selected such that the lever arms resist bending away from the position shown. Annular base 360 is designed to mate to the distal end of cavity 332 to secure spring 306 in position with lever arms 362 held perpendicular to the longitudinal axis of bone anchor 324 in the unloaded state.

Housing 330 is similar to housing 230 with the exception that a short column 334 extends up from the distal end of cavity 332 into cavity 332. As shown in FIGS. 3B and 3C, a column 334 in the distal end of cavity 332 of housing 330 is sized to fit within aperture 365 of spring 306. Column 334 has a curved indentation 335 at the proximal end for receiving nub 248 of deflectable post 204. Retainer 202 is positioned within cavity 332 such that nub 248 engages curved indentation 335 of column 334. Thus retainer 202 is trapped between column 334 and collar 210 and may pivot about a pivot point within nub 248. Collar 210 is secured to the proximal end of cavity 332 thereby securing retaining 202 in cavity 332 and trapping spring 306 between retainer 202 and housing 330.

Spring 306 is received around column 334 at the distal end of cavity 332. The stiffness of deflection rod 300 is affected by the spring rate of spring 306. The stiffness of the deflection rod 300 can be changed for example by increasing the spring rate of lever arms 362 of spring 306 and conversely the stiffness may be reduced by decreasing the spring rate of spring 306. The spring rate of the lever arms 362 of spring 206 can be, for example, increased by increasing the thickness of the lever arms 362 and/or decreasing the length of the lever arms 362. Alternatively and/or additionally changing the materials of the spring 306 can also affect the spring rate. For example, making spring 306 out of stiffer material increases the spring rate and thus reduces deflection of deflectable post 304 for the same amount of load—all other factors being equal. Spring 306 is preferably made of a biocompatible polymer or metal. Spring 306 may, for example, be made from PEEK, Bionate®, Nitinol, steel and/or titanium.

Referring now to FIGS. 3B and 3C, which show sectional views of a fully assembled deflection rod 300. When assembled, spring 306 is positioned in the distal end of cavity 332 of housing 330. Retainer 202 is inserted into cavity 330 so that nub 248 of retainer 202 engages indentation 335 of housing 330. Ridge 226 of retainer 202 makes contact with lever arms 362. Collar 310 is positioned over deflectable post 204 and secured into the threaded opening of cavity 332. Collar 232 has a curved surface 212 which is complementary to the curved surface 240 of retainer 202. Collar 210 secures retainer 202 within cavity 230 and traps spring 306 between retainer 202 and housing 330.

Deflectable post 204 may pivot about nub 248. When assembled, deflectable post 204 may pivot about the center of rotation defined by engagement of nub 248 with curved indentation 335 in FIGS. 3A, 3B. Deflectable post 204 may also rotate about its longitudinal axis. FIG. 3B shows a partial sectional view of a fully assembled deflection rod 300. As shown in FIG. 3B, spring 306 occupies the space between retainer 202 and housing 330. When deflectable post 204 deflects from a position coaxial with bone anchor 320, ridge 226 pushes on spring 306 compressing spring 306. The spring 306 is compressed in a direction parallel to the axis of bone anchor 320. To put it another way a load applied transverse to the axis of the deflectable post 304 is absorbed by compression of spring 306 in a direction generally parallel to the axis of bone anchor 320.

As shown in FIG. 3C, when deflectable post 204 deflects away from alignment with bone anchor 324, retainer 202 compresses spring 206 between retainer 202 and housing 230. Spring 206 is compressed in a direction parallel to the longitudinal axis of bone anchor 324. After a fixed amount of deflection, deflectable post 204 makes contact with collar 210. FIG. 3C illustrates deflection of deflectable post 204. Applying a transverse load to deflectable post 204 causes deflection of deflectable post 204 relative to shield 208 (and any bone anchor to which it may be mounted). Initially deflectable post 204 pivots about a pivot point indicated by an X. In this embodiment, the pivot point is located at the center of nub 248. In other embodiments, however, the pivot point may be positioned at a different location. For example, for other retainer shapes disclosed in the applications incorporated by reference herein, the retainer may pivot about a point which is at the edge of the retainer or even external to the retainer. As shown in FIG. 3C, deflection of deflectable post 204 deforms the spring 306. The force required to deflect deflectable post 204 depends upon the dimensions of deflectable post 204, spring 306 as well as the attributes of the material of spring 306. In particular, the spring rate of spring 306 and lever arms 362 thereof (See FIG. 3A) may be adjusted to impart the desired force-deflection characteristics to deflectable post 204.

Figure 4A:
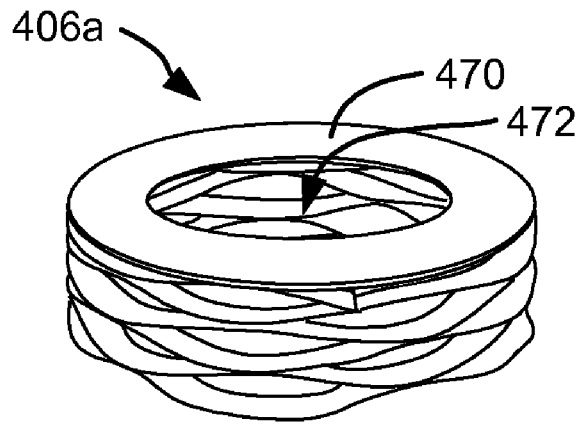
FIG. 4A through 4C show alternative spring designs which may be utilized in deflection rod of the present invention.
Figure 4B:
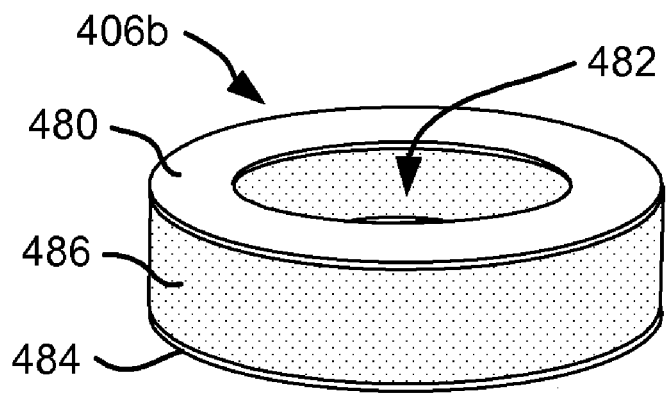
Figure 4C:
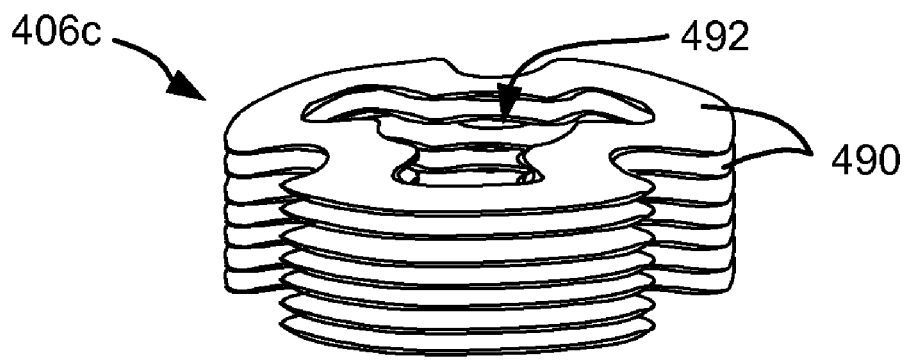

The spring/spring elements in the deflection rod of FIGS. 3A-3C are designed to elastically deform in the longitudinal direction (relative to deflectable post 204 and bone anchor 320). Alternative designs of springs may be used to control deflection of deflectable post 204 including, for example, spring washers, Belleville washers/disc springs, CloverDome™ spring washers, CloverSprings™, conical washers, wave washers, coil springs and finger washers. Examples of alternative springs which may be used in the deflection rod of FIGS. 3A-3C are shown in FIGS. 4A-4C FIG. 4A shows an alternative annular spring 406a which may be used in place of spring 306 of FIGS. 3A-3C. As shown in FIG. 4A, spring 406a is a multi-turn wave spring having an attached end plate 370. Spring 406a has a central aperture 472 sized to fit over column 334 of housing 330 (see, e.g. FIGS. 3B, 3C). Spring 406a may be manufactured such that when uncompressed it is slightly longer than the gap between retainer 202 and housing 330. Thus, spring 406a is preloaded when assembled with bone anchor 320. This reduces any slack that may occur in the force deflection response of deflectable post 204 even if there is some relaxation of spring 406a after assembly. Wave springs having on or more turns are advantageous in this application in that they may be design to have a high spring constant relative to the size of the spring and range of travel. The thickness of the metal, the number of turns of the spring and other dimensions may be are selected based upon the spring constant and range of deflection desired. An end plate 470 as shown may be used to ensure that the force deflection characteristics of the deflection rod are isotropic and independent of whether the direction of deflection is coincident with the peak or trough of the wave spring.

FIG. 4B shows an alternative annular spring 406b which may be used in place of spring 306 of FIGS. 3A-3C. As shown in FIG. 4B, spring 406b has a ring of compliant polymer 486 sandwiched between end plates 480 and 484. Spring 406b has a central aperture 482 sized to fit over column 334 of housing 330 (see, e.g. FIGS. 3B, 3C). Spring 406*b* may be manufactured such that when uncompressed it is slightly longer than the gap between retainer 202 and housing 330. Thus, spring 406*b* is preloaded when assembled with bone anchor 320. This reduces any slack that may occur in the force deflection response of deflectable post 204 even if there is some relaxation of spring 406*b* after assembly. The material of compliant polymer ring 486 may be selected to generate the desired spring constant. End plate 480 may be used to protect the ring of compliant polymer 486 from wear caused by motion of retainer 202. End plate 484 is designed to engage the distal end of cavity 332, and secure compliant polymer ring 486 in position. In some embodiments, the compliant polymer ring may be utilized without one or more of end plates 484 and 480.

A number of designs of spring washers are suitable for use in deflection rod 300 of FIGS. 3A-3C. For example, FIG. 4C shows a clover spring washer 406*c*. The washer 406*c* is a type of domed spring washer with cutouts that increase the compliance. The clover spring and or other spring washers may be designed to provide the desired spring constant and deflection characteristics. One or more spring washers 406*c* may be stacked to increase the spring constant. In some embodiments, a different number of spring washers may be utilized in different versions of the deflection rod in order to easily manufacture a range of deflection rods having different force/deflection characteristics. Alternatively, the dimensions of the washers may be selected to generate washers having the desired spring constant and range of deflection. Although a clover spring washer is shown, other spring washers such as Belleville washers, finger washers, conical washers, dome washers may be used in the deflection rod of FIGS. 3A-3C. FIG. 4C shows an alternative annular spring system 406*c* which may be used in place of spring 306 of FIGS. 3A-3C.

As shown in FIG. 4C, spring system 406*c* includes a stack of spring washers 490. Each spring washer 490 has a central aperture 492 sized to fit over column 334 of housing 330 (see, e.g. FIGS. 3B, 3C). Spring system 406*c* may be designed such that when uncompressed it is slightly longer than the gap between retainer 202 and housing 330. Thus, spring 406*c* is preloaded when assembled with bone anchor 320. This reduces any slack that may occur in the force deflection response of deflectable post 204 even if there is some relaxation of spring 406*c* after assembly. The material and configuration of spring washers 490 may be selected to generate the desired spring constant. Although a cloverleaf design spring washer is shown alternative configurations of spring washers including, for example, dome washers, Belleville washers, and/or finger washers may be utilized to achieve the desired force deflection characteristics. Typically the spring washer will be formed of a biocompatible metal, for example steel or titanium.

Figure 5A:
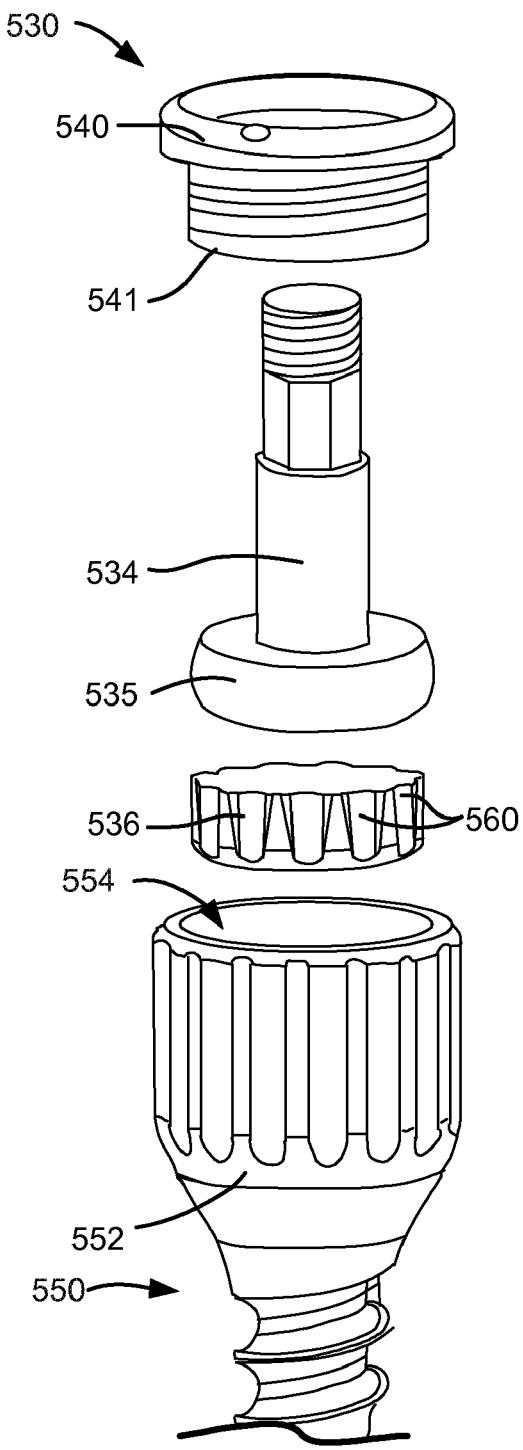
FIG. 5A is an exploded view of an alternative deflection rod according to an embodiment of the present invention.
Figure 5B:
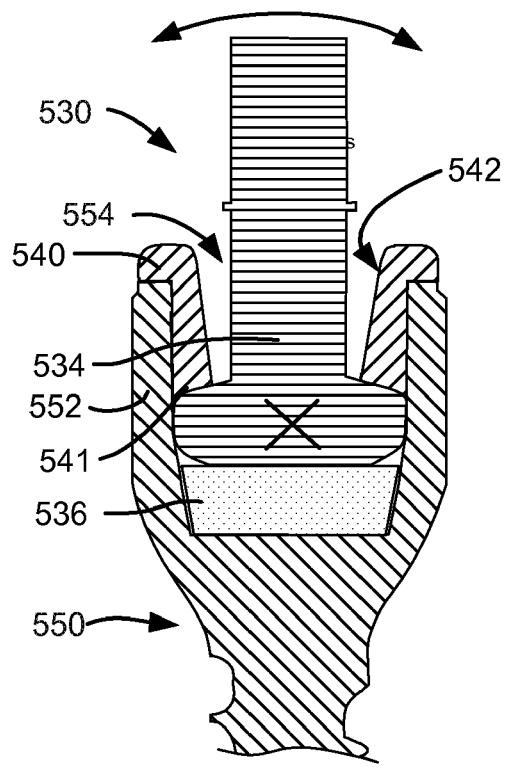
FIGS. 5B and 5C are sectional views of the deflection rod of FIG. 5A.
Figure 5C:
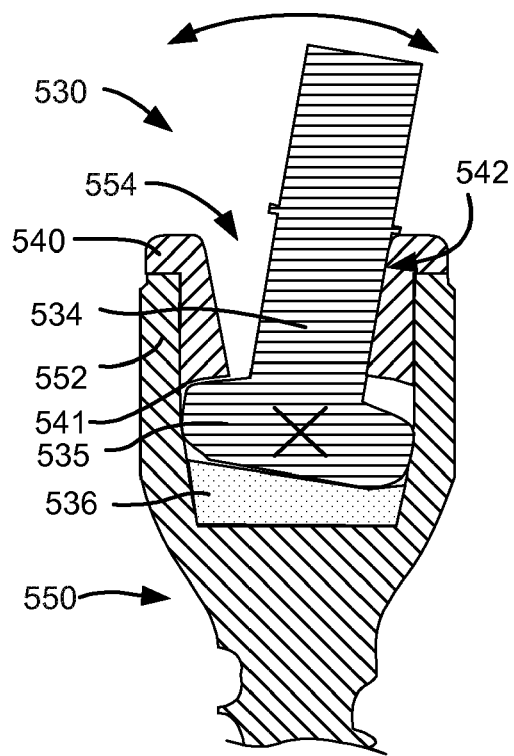

FIGS. 5A-5C show views of an alternative deflection rod 530 according to an embodiment of the invention. FIG. 5A shows an exploded view of the deflection rod 530. FIGS. 5B and 5C show sectional views of the deflection rod 530 with FIG. 5C illustrating deflection of deflection rod 530 under load.

Referring first to FIG. 5A, deflection rod 530 is assembled in cavity 554 of housing 552 of bone anchor 550. A compliant disc 536 is first placed into cavity 554. With compliant disc 536 in position, deflectable post 534 is then inserted into cavity 554. Deflectable post 534 has a retainer in the form of control disc 535 at the distal end. Control disc 535 fits snuggly against compliant disc 536. Collar 540 is then secured into the end of cavity 554 by threads or the like. Collar 540 may also be bonded or welded into place. The lower surface 541 of collar 540 is shaped to form the top portion of a pocket in which control disc 535 may pivot and rotate. The edges of control disc 535 and the walls of cavity 554 are radiussed so that control disc 535 may pivot over the desired range of travel. The edges of control disc 535 and the walls of cavity 554 interact to maintain the center of rotation of the control disc 535 in a fixed position (shown by the X in FIGS. 5B and 5C).

Compliant disc 536 is preferably made of a compliant biocompatible polymer. Compliant disc 536 may, for example, be made from a polycarbonate urethane (PCU) such as Bionate®. If the compliant disc 536 is comprised of Bionate®, a polycarbonate urethane or other hydrophilic polymer, the compliant disc 536 can also act as a fluid-lubricated bearing for rotation of the deflectable post 534 relative to the longitudinal axis of the deflectable post 534. In an embodiment, the compliant disc 536 is made of PCU, is 2 mm thick when uncompressed and may be compressed to about 1 mm in thickness by deflection of the post.

As shown in FIG. 5A, compliant disc 536 may be provided with voids and or relief to modulate response of the compliant disc 536 to compression by the control disc 535. As shown in FIG. 5A, compliant disc 536 is provided with a plurality of grooves 560 in the outer surface. The material of compliant disc 536 may expand to fill these grooves when compressed by controlled disc 536. Such feature may also serve to reduce wear upon the compliant disc and prevent pinching of compliant disc 536 between control disc 535 and housing 552. The compliant disc 536 may also include polymer regions having different properties. For example, the compliant disc 536 can include localized regions having one or more polymers with each region having a different hardness of stiffness or durometer. For example, regions in different directions from the center can have a higher hardness or stiffness or durometer so that as the deflectable post 534 is deflected outwardly from a position that is collinear with the longitudinal axis the compliant disc 536 provides more resistance to deflection in some directions as compared to others (an anisotropic force-deflection response). In alternative embodiments, a spring may be used in place of compliant disc 536. For example one or more wave springs or spring washer may be used in place of compliant disc 536.

FIG. 5B shows a sectional view of deflection rod 530 when fully assembled. As shown in FIG. 5B control disc 535 sits on top of compliant disc 536 within cavity 554 of housing 552. Control disc 535 is secured in a pocket formed by the walls of cavity 554 and collar 540. Deflectable post 534 may pivot in any direction and rotate about its long axis. However, as shown in FIG. 5C, when deflectable post 534 pivots, control disc 535 also pivots compressing the material of compliant disc 536. Compression of compliant disc 536 by control disc 535 imparts the deflectable post 534 with a controllable force/load response which can be customized as previously described. A limit surface 542 of collar 540 is designed to make contact with deflectable post 534 after a predetermined amount of deflection. Further deflection of the proximal end of deflectable post 534 after contact with limit surface 542 requires bending of deflectable post 534. Thus the stiffness of deflectable rod 530 will typically increase dramatically upon contact between deflectable post 534 and limit surface 542.

FIGS. 6A-6C illustrate an alternative deflection rod 600. FIG. 6A shows an exploded view of alternative deflection rod 600. Deflection rod 600 includes retainer 602, deflectable post 604, spring 606, collar 610, and mount 614. Deflection rod 600 is assembled with a bone anchor 620. Bone anchor 620 includes a threaded bone anchor 624 having a housing 630 at the proximal end. Housing 630 contains a cavity 632 which is coaxial with bone anchor 624. Deflection rod 600 is assembled within cavity 632 such that deflectable post 604 is generally coaxial or collinear with the longitudinal axis of bone anchor 624 when not loaded. In this embodiment, spring 606 is trapped in cavity 632 between retainer 602 and collar 610. The deflectable post 604 is configured so that deflection of the deflectable post 604 causes compression of spring 606 in a direction generally parallel to the axis of bone anchor 620. (See, e.g. FIGS. 6B & 6C). Retainer 602 is hemispherical and is received in a hemispherical pocket 634 in the distal end of cavity 632.

FIGS. 6B and 6C show a sectional view of deflection rod 600 as assembled. Retainer 602 is positioned within cavity 632 such that it engages curved distal end 634 of cavity 632. Spring 606 is received around deflectable post 604. Collar 610 is secured to the proximal end of cavity 632 thereby trapping spring 606 between collar 610 and the flat upper surface 603 of retainer 602. Deflectable post 604 may pivot about pivot point 638. As shown in FIG. 6C, when deflectable post 604 deflects away from alignment with bone anchor 620, retainer 602 compresses spring 606 between retainer 602 and collar 610. Spring 606 is compressed in a direction parallel to the longitudinal axis of bone anchor 620.

As shown in FIG. 6C, after further deflection, deflectable post 604 comes into contact with limit surface 672 of collar 610. Limit surface 672 is oriented such that when deflectable post 604 makes contact with limit surface 672, the contact is distributed over an area to reduce stress on deflectable post 604 and limit surface 672. As depicted, the limit surface 672 is configured such that as the deflectable post 604 deflects into contact with the limit surface 672, the limit surface 672 is aligned/flat relative to the deflectable post 604 in order to present a larger surface to absorb any load an also to reduce stress or damage on the deflectable.

Additional deflection of deflectable post 604 after contact with limit surface 672 may cause elastic deformation (bending) of deflectable post 604. Because deflectable post 604 is relatively stiff, the force required to deflect deflectable post 604 increases significantly after contact of deflectable post 604 with the limit surface 672. For example, the stiffness may double upon contact of the deflectable post 604 with the limit surface 672 of collar 610. In a preferred embodiment, the proximal end of deflectable post 604 may deflect from 0.5 mm to 2 mm before deflectable post 604 makes contact with limit surfaces 672. More preferably deflectable post 604 may deflect approximately 1 mm before making contact with limit surface 672.

Thus as load or force is first applied to the deflection rod by the spine, the deflection of the deflection rod 600 responds about linearly to the increase in the load during the phase when deflection of deflectable post 604 causes compression of spring 606 as shown in FIG. 6C. After about 1 mm of deflection, when deflectable post 604 contacts limit surface 672 the deflection rod 600 becomes stiffer. Thereafter a greater amount of load or force needs to be placed on the deflection rod in order to obtain the same incremental amount of deflection that was realized prior to this point because further deflection requires bending of deflectable post 604. Accordingly, the deflection rod 600 provides a range of motion where the load supported increases about linearly as the deflection increases and then with increased deflection the load supported increases more rapidly in order to provide stabilization. To put it another way, the deflection rod 600 becomes stiffer or less compliant as the deflection/load increases.

The spring/spring elements in the deflection rod of FIGS. 6A-6C are designed to elastically deform in the longitudinal direction (relative to deflectable post 604 and bone anchor 620). The spring 606 shown in FIGS. 6A-6C is a multi-turn wave spring. Alternative designs of springs may be used to control deflection of deflectable post 604 including, for example, spring washers, Belleville washers/disc springs, CloverDome™ spring washers, CloverSprings™, conical washers, wave washers, coil springs and finger washers. Examples of alternative springs which may be used in the deflection rod of FIGS. 6A-6C are shown in FIGS. 4A-4C. As previously suggested the spring 606 may be designed to be slightly longer than the space between the retainer 602 and the collar 610 in order to preload the spring and limit or preclude slack. A large preload force from spring 606 may also be useful to secure retainer 602 within pocket 634.

Figure 7A:
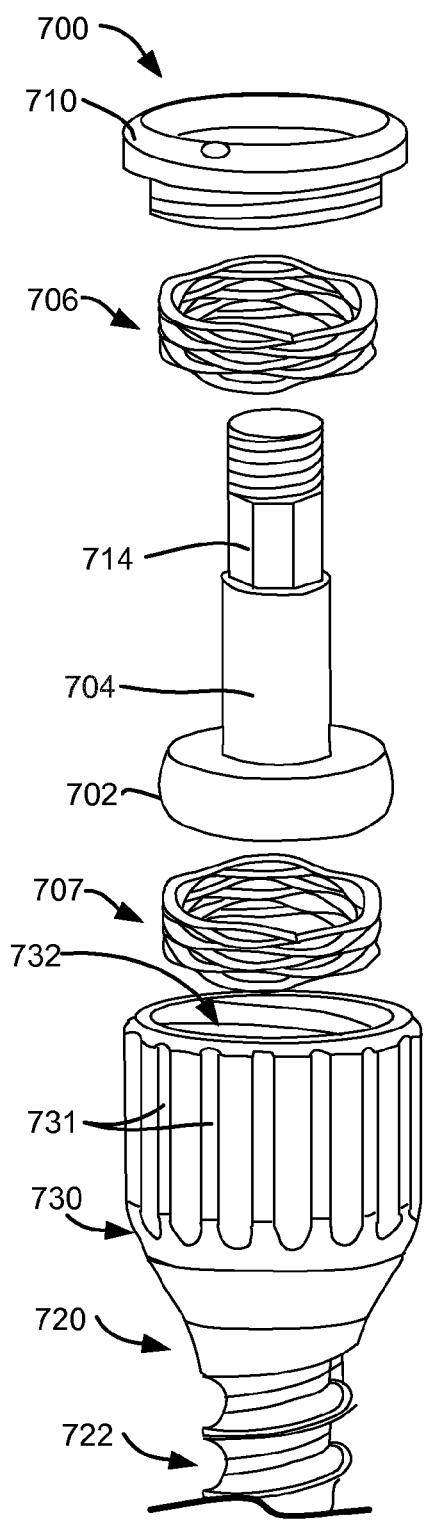
FIG. 7A is an exploded view of an alternative deflection rod according to an embodiment of the present invention.
Figure 7B:
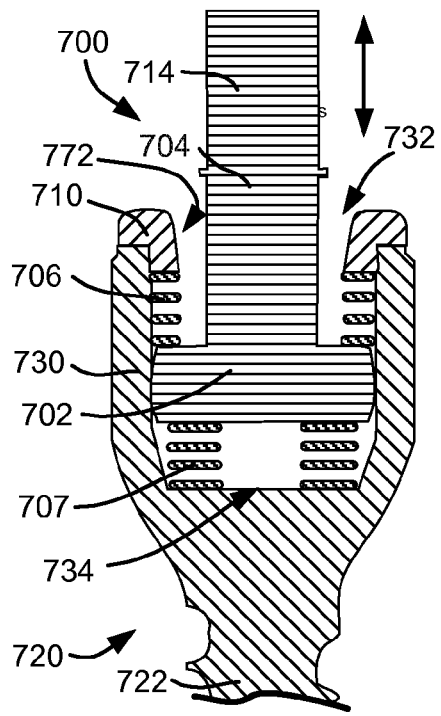
FIGS. 7B and 7C are sectional views of the deflection rod of FIG. 6A.
Figure 7C:
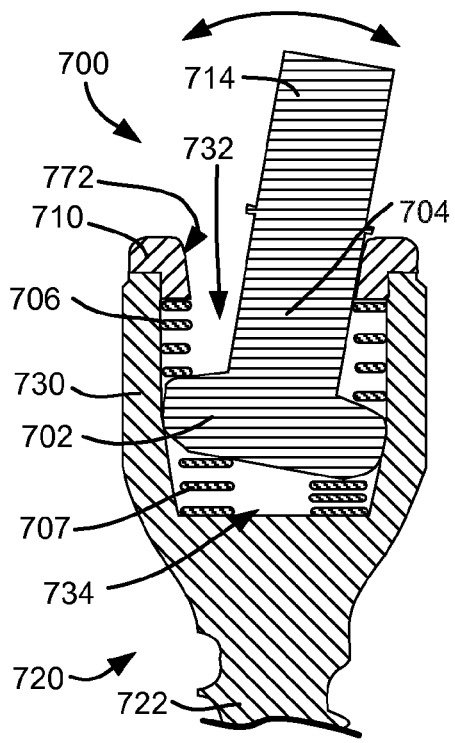

FIGS. 7A-7C illustrate an alternative deflection rod 700. FIG. 7A shows an exploded view of alternative deflection rod 700. Deflection rod 700 includes retainer 702, deflectable post 704, spring 706, spring 707, collar 710, and mount 714. Deflection rod 700 is assembled with a bone anchor 720. Bone anchor 720 includes a threaded bone anchor 724 having a housing 730 at the proximal end. Housing 730 contains a cavity 732 which is coaxial with bone anchor 724. Deflection rod 700 is assembled within cavity 732 such that deflectable post 704 is generally coaxial or collinear with the longitudinal axis of bone anchor 724 when not loaded. In this embodiment, spring 706 is trapped in cavity 732 between retainer 702 and collar 710 and spring 707 is trapped between retainer 702 and the distal end of cavity 732. The deflectable post 704 is configured so that deflection of the deflectable post 704 causes compression of springs 706 & 707 in a direction generally parallel to the axis of bone anchor 720. (See, e.g. FIGS. 7B & 7C).

Retainer 702 is generally disc shaped and is received between spring 706 & 707 in cavity 732. Springs 706 and 707 need not be identical but preferably have similar spring rates. The spring/spring elements in the deflection rod of FIGS. 7A-7C are designed to elastically deform in the longitudinal direction (relative to deflectable post 704 and bone anchor 720). The springs 706, 707 shown in FIG. 7A are multi-turn wave springs. Alternative designs of springs may be used to control deflection of deflectable post 704 including, for example, spring washers, Belleville washers/disc springs, CloverDome™ spring washers, CloverSprings™, conical washers, wave washers, coil springs and finger washers. Examples of alternative springs which may be used in the deflection rod of FIGS. 7A-7C are shown in FIGS. 4A-4C. As previously suggested the springs 706 & 707 may be designed to be slightly longer than the space between the retainer 702, collar 710 and the distal end of cavity 732. The springs 706, 707 must then be compressed during assembly which preloads the spring and limits or precludes slack. A large preload force from springs 706 and 707 may also be useful to hold retainer 702 at a desired position within pocket 734.

FIGS. 7B and 7C show a sectional view of deflection rod 700 as assembled. Spring 707 is first place in cavity 732. Retainer 702 is positioned within cavity 732. Spring 706 is then placed over deflectable post 704. Collar 710 is secured to the proximal end of cavity 732 thereby trapping spring 706 between collar 710 and upper surface of retainer 702 and trapping spring 707 between the lower surface of retainer 702 and the distal end of cavity 732. Deflectable post 704 may pivot about cavity 732. As shown in FIG. 7C, when deflectable post 704 deflects away from alignment with bone anchor 720, retainer 702 compresses springs 706 and 707 between retainer 702 and collar 710 and distal end of cavity 732.

Springs 706 and 707 are compressed in a direction parallel to the longitudinal axis of bone anchor 720.

As shown in FIG. 7C, after further deflection, deflectable post 704 comes into contact with limit surface 772 of collar 710. Limit surface 772 is oriented such that when deflectable post 704 makes contact with limit surface 772, the contact is distributed over an area to reduce stress on deflectable post 704 and limit surface 772. As depicted, the limit surface 772 is configured such that as the deflectable post 704 deflects into contact with the limit surface 772, the limit surface 772 is aligned/flat relative to the deflectable post 704 in order to present a larger surface to absorb any load an also to reduce stress or damage on the deflectable.

Additional deflection of deflectable post 704 after contact with limit surface 772 may cause elastic deformation (bending) of deflectable post 704. Because deflectable post 704 is relatively stiff, the force required to deflect deflectable post 704 increases significantly after contact of deflectable post 704 with the limit surface 772. For example, the stiffness may double upon contact of the deflectable post 704 with the limit surface 772 of collar 710. In a preferred embodiment, the proximal end of deflectable post 704 may deflect from 0.5 mm to 2 mm before deflectable post 704 makes contact with limit surfaces 772. More preferably deflectable post 704 may deflect approximately 1 mm before making contact with limit surface 772.

Thus as load or force is first applied to the deflection rod by the spine, the deflection of the deflection rod 700 responds about linearly to the increase in the load during the phase when deflection of deflectable post 704 causes compression of spring 706 as shown in FIG. 7C. After about 1 mm of deflection, when deflectable post 704 contacts limit surface 772 the deflection rod 700 becomes stiffer. Thereafter a greater amount of load or force needs to be placed on the deflection rod in order to obtain the same incremental amount of deflection that was realized prior to this point because further deflection requires bending of deflectable post 704. Accordingly, the deflection rod 700 provides a range of motion where the load supported increases about linearly as the deflection increases and then with increased deflection the load supported increases more rapidly in order to provide stabilization. To put it another way, the deflection rod 700 becomes stiffer or less compliant as the deflection/load increases.

Alternative Bone Anchors

Figure 8A:
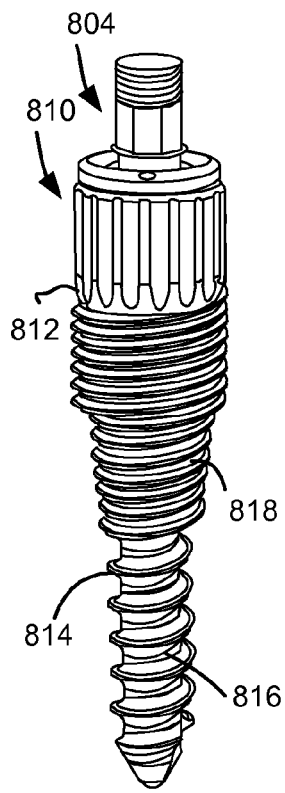
FIGS. 8A-8E are perspective views of alternative combinations of deflection rods and bone anchors according to embodiments of the present invention.

FIGS. 8A though 8E illustrate some possible variations in bone anchors of the anchoring system. The bone anchors each have a housing compatible with the deflection rods of the deflection system and the offset heads/connectors of the connector system. In some embodiments, the deflection rod is installed/assembled in the bone anchor prior to implantation of the bone anchors in the body. In alternative embodiments, the bone anchors may be implanted in the body before installation of a deflection rod.

Bone anchor 810 of FIG. 8A is a bone anchor having a threaded region 814 which extends up over most of a housing 812. A deflection rod 804 is installed in housing 812. The threaded region 814 may extend over a greater or lesser amount of housing 812 depending upon such factors as the length of the bone anchor, the type of bone in which the screw is to be implanted and the desired height to which the housing 812 will extend above the bone surface after implantation. Bone anchor 810 may be useful to lower the depth of the pivot point of the deflection rod 804 closer to the natural instantaneous center of rotation of the spine. Note also that the distal thread depth 816 may be deeper than the proximal thread depth 818. The distal threads 818 are adapted for engagement of the soft cancellous bone while the proximal threads is adapted for engagement of the harder cortical bone at the surface of the vertebra.

Figure 8B:
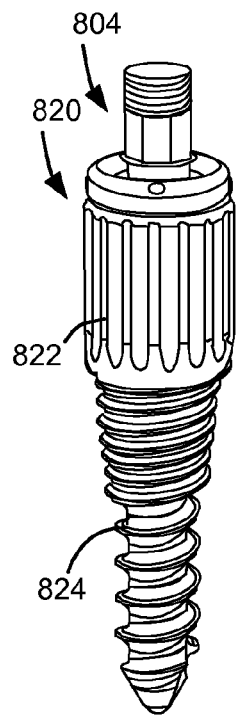

Bone anchor 820 of FIG. 8B is a bone anchor in which the screw-only section 824 is shorter in length than in bone anchor 810 of FIG. 8A. A deflection rod 804 is installed in housing 822. Different lengths of screw-only section may be useful in different patients or different vertebrae as the size of the bone in which the anchor needs be implanted may vary considerably. For example short bone anchors are desirable where the dynamic stabilization system is to be implanted in smaller vertebrae. The physician may determine the length of bone anchor appropriate for a particular patient by taking measurements during the procedure of by determining measurements from non-invasive scanning, for example, X-ray NMR, and CT scanning. Note however, that housing 822 is preferably the same size and shape as the housings of the other bone anchors so as to be compatible with the same deflection rods, components and connectors.

Figure 8C:
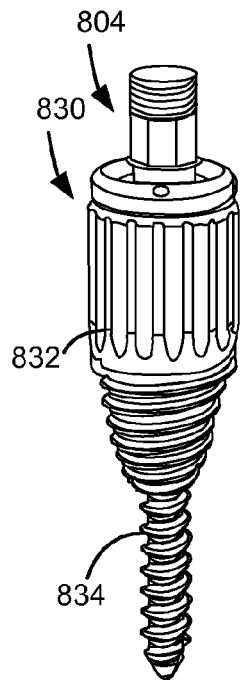

Bone anchor 830 of FIG. 8C is a bone anchor in which the screw-only section 834 has a smaller diameter and is shorter in length than in bone anchor 810 of FIG. 8A. A deflection rod 804 is installed in housing 832. Different diameters of screw-only section may be useful in different patients or different vertebrae as the size of the bone in which the anchor needs be implanted may vary considerably. For example smaller diameter bone anchors may be desirable where the dynamic stabilization system is to be implanted in smaller vertebrae. The physician may determine the diameter of bone anchor appropriate for a particular patient by taking measurements during the procedure of by determining measurements from non-invasive scanning, for example, X-ray NMR, and CT scanning. Note however, that housing 832 is preferably the same size and shape as the housings of the other bone anchors so as to be compatible with the same deflection rods, components and connectors.

Figure 8D:
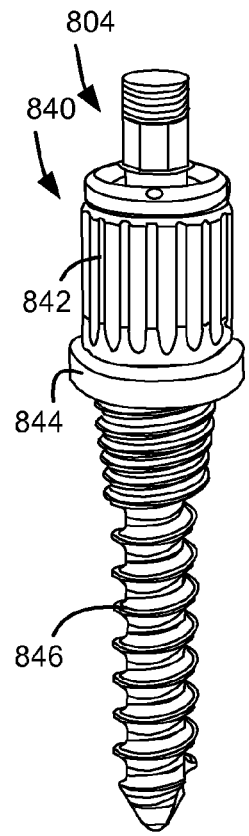

Bone anchor 840 of FIG. 8D is a bone anchor in which the housing 842 has a rim 844 extending away from housing 842 where it transitions to the threaded region 846. A deflection rod 804 is installed in housing 842. Rim 844 may serve to retain an offset head mounted to housing 842 in a way that it can rotate freely around housing 842 during installation. Rim 844 may also serve to widen the contact area between the bone anchor 840 where it meets the bone of the vertebra. This can act as a stop preventing over-insertion. This can also provide a wide base for stabilizing the housing against lateral motion and torque. Note that housing 842 is preferably the same size and shape as the housings of the other bone anchors so as to be compatible with the same deflection rods and connectors.

Figure 8E:
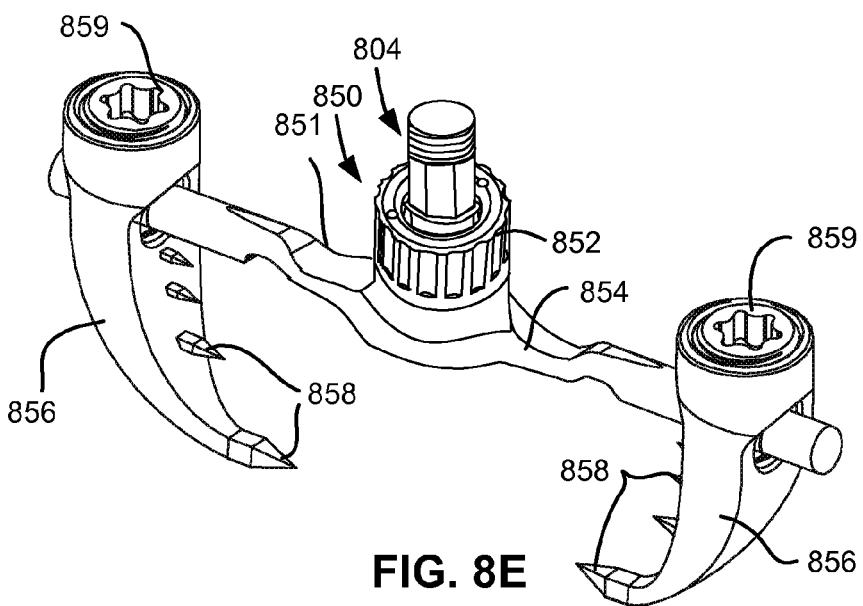

Bone anchor 850 of FIG. 8E illustrates a bone hook device 851 having a housing 852. A deflection rod 804 is installed in housing 852. Bone hook device 851 comprises a bar 854 to which housing 852 is rigidly connected. At either end of bar 854 is a bone hook 856 having a set screw 857 for securing the bone hook 856 to the bar 854. Each bone hook 856 has a plurality of sharp points 858 for engaging and securing the bone hook 856 to a vertebra. During use, the bone hooks 856 are urged towards each other until the sharp points engage and/or penetrate the surface of a bone. Set screws 857 are tightened to secure bone hooks 856 in position relative to bar 854 and thus secure housing 852 relative to the bone. Different arrangements of bone hooks and bars may be made suitable for attachment of the housing 852 to different types, sizes, shapes and locations of vertebra. Note that housing 852 is preferably the same size and shape as the housings of the other bone anchors so as to be compatible with the same deflection rods, components and connectors.

Deflection Rod/Loading Rod Materials

Movement of the deflectable post relative to the bone anchor provides load sharing and dynamic stabilization properties to the dynamic stabilization assembly. As described above, deflection of the deflectable post deforms the material of the spring. The spring applies a restoring force upon the deflectable post the force being dependent upon the spring rate of the spring and the amount of deflection of the deflectable post. The design, dimensions and the material of the spring may be selected to achieve the desired spring rate. The characteristics of the spring in combination with the dimensions of the other components of the deflection rod interact to generate the force-deflection curve of the deflection rod.

The design, dimensions and materials may be selected to achieve the desired force-deflection characteristics. By changing the dimensions of the deflectable post, spring and spring elements the deflection characteristics of the deflection rod can be changed. The stiffness of components of the deflection rod can be, for example, increased by increasing the diameter of the deflectable post. Additionally, decreasing the diameter of the deflectable post will decrease the stiffness of the deflection rod. Alternatively and/or additionally changing the materials which comprise the components of the deflection rod can also affect the stiffness and range of motion of the deflection rod. For example, making the spring out of stiffer and/or harder material increases the load necessary to cause a given deflection of the deflection rod.

The deflectable post, bone anchor and vertical rods are preferably made of biocompatible implantable metals. The deflectable post can, for example, be made of, titanium, a shape memory metal for example Nitinol (NiTi) or stainless steel. In preferred embodiments the deflectable post is made of titanium. In preferred embodiments the bone anchor and vertical rods are also made of titanium; however, other materials for example stainless steel may be used instead of or in addition to the titanium components.

The spring can be formed by extrusion, injection, compression molding and/or machining techniques, as would be appreciated by those skilled in the art. In some embodiments, the spring is formed separately. For example, a spring may be cut or machined from a biocompatible polymer and then assembled with the deflectable post and spring such as by being press fit into the shield. Alternatively or additionally, a fastener or biocompatible adhesive may be used to secure the spring to the shield and/or post.

The material of the spring is preferably a biocompatible and implantable polymer or metal having the desired deformation characteristics—elasticity and modulus. The material of the spring should also be able to maintain the desired deformation characteristics. Thus the material of the spring is preferably durable, resistant to oxidation and dimensionally stable under the conditions found in the human body. The spring may, for example be made from a PEEK or a polycarbonate urethane (PCU) such as Bionate® or a surgical steel or titanium or Nitinol. If the spring is comprised of Bionate®, a polycarbonate urethane or other hydrophilic polymer, the spring can also act as a fluid-lubricated bearing for rotation of the deflectable post relative to the longitudinal axis of the deflectable post.

Other polymers or thermoplastics may be used to make the spring including, but not limited to, polyether-etherketone (PEEK), polyphenylsolfone (Radel®), or polyetherimide resin (Ultem®). Other polymers that may be suitable for use in some embodiments, for example other grades of PEEK, for example 30% glass-filled or 30% carbon filled, provided such materials are cleared for use in implantable devices by the FDA, or other regulatory body. Glass-filled PEEK is known to be ideal for improved strength, stiffness, or stability while carbon filled PEEK is known to enhance the compressive strength and stiffness of PEEK and lower its expansion rate.

Still other suitable biocompatible thermoplastic or thermoplastic polycondensate materials may be be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further, other polyketones can be used as well as other thermoplastics.

Still other polymers that can be used in the spring are disclosed in the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The design, dimensions and materials of the spring are selected in combination with the design of the deflection rod to create a deflection rod having stiffness/deflection characteristics suitable for the needs of a patient. By selecting appropriate spring and spring rate the deflection characteristics of the deflection rod can be configured to approach the natural dynamic motion of the spine of a particular patient, while giving dynamic support to the spine in that region. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine. Note also, as described above, in certain embodiments, a limit surface cause the stiffness of the deflection rod to increase after contact between the deflectable post and the limit surface.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A dynamic spine stabilization device comprising:
   a bone anchor having a housing and a longitudinal axis;
   a cavity in the housing coaxial with the longitudinal axis;
   a post received in the cavity;
   the post having a retainer at a distal end and a mount at a proximal end;
   the retainer being secured in a pocket of the cavity of the housing such that the post may be deflected within the housing;
   a spring positioned in the cavity of the housing between the post and the housing such that deflection of the post causes compression of the spring in a direction parallel to the longitudinal axis; and
   wherein the spring applies a force upon the post pushing the post towards a position in which the post is coaxial with the longitudinal axis.

2. The device of claim 1, wherein said spring comprises a plurality of lever arms arranged in a circle.

3. The device of claim 1, wherein said spring comprises a plurality of planar spring elements.

4. The device of claim 1, wherein said housing has a limit surface which contacts the post upon deflection of said post a first amount from the position in which the longitudinal axis of the post is coaxial with the bone anchor.

5. The device of claim 1, wherein:
said housing has a limit surface which contacts the post upon deflection of said post a first amount from the position in which the longitudinal axis of the post is coaxial with the bone anchor; and
wherein further deflection of said post beyond said first amount requires a larger load per unit of deflection than deflection of said post up to said first amount.

6. The device of claim 1, wherein:
said housing has a limit surface which contacts the post upon deflection of said post a first amount from the position in which the longitudinal axis of the post is coaxial with the bone anchor; and
wherein further deflection of said post beyond said first amount requires at least double the load per unit of deflection than deflection of said post up to said first amount.

7. The device of claim 1, wherein said post can be deflected about a point in said bone anchor that is adapted to be implanted adjacent a surface of a vertebra.

8. The device of claim 1, wherein said spring has an isotropic deflection profile.

9. The device of claim 1, wherein said spring has an anisotropic deflection profile.

10. The device of claim 1 wherein during deflection the post first is urged against said spring and then is subsequently urged against a limit surface of said housing.

11. The device of claim 1, wherein the spring includes a plurality of arms that extend perpendicularly to the post.

12. A spine stabilization device comprising:
a bone anchor having a distal end adapted to engage a bone;
a housing at a proximal end of said bone anchor;
a longitudinal bore in said housing;
said bore being aligned with the bone anchor and having an open end and a closed end;
a deflectable post having a proximal end, an elongated body and a distal end;
the proximal end of said deflectable post extending from the open end of said longitudinal bore;
a curved retainer at the distal end of the deflectable post;
the curved retainer being received in the longitudinal bore;
a fastener which secures the curved retainer in the longitudinal bore but allows the deflectable post to pivot relative to the bone anchor; and
a spring positioned within the bore between the deflectable post and the housing such that the spring flexibly resists pivoting of the deflectable post towards the housing wherein pivoting of the deflectable post causes compression of the spring in a direction parallel to the axis of the longitudinal bore.

13. The spine stabilization device of claim 12, further comprising:
a limit surface associated with the housing and positioned to contact the deflectable post after a first angle of pivoting of the deflectable post away from alignment with the bone anchor; and
wherein the limit surface resists further pivoting of said deflectable post beyond said first angle.

14. The spine stabilization device of claim 12, further comprising:
a limit surface associated with the housing and positioned to contact the deflectable post after a first angle of pivoting of the deflectable post away from alignment with the bone anchor; and
wherein deflection of the proximal end of the deflectable post after contact between the deflectable post and the limit surface requires at least double the load per unit of deflection than deflection of said post prior to contact between the deflectable post and the limit surface.

15. The spine stabilization device of claim 12, wherein said spring is made of PEEK.

16. The spine stabilization device of claim 12, wherein the spring comprises a first portion in contact with the deflectable post, a second portion in contact with the housing and a flexible portion between the first portion and the second portion which is elastically deformed by pivoting of the deflectable post towards the housing.

17. The spine stabilization device of claim 12, wherein the spring comprises a first portion in contact with the deflectable post, a second portion in contact with the housing and a flexible portion between the first portion and the second portion which is elastically deformed by pivoting of the deflectable post towards the housing and wherein the third portion comprises a plurality of lever arms.

18. The spine stabilization device of claim 12, wherein the spring comprises a first portion in contact with the deflectable post, a second portion in contact with the housing and a flexible portion between the first portion and the second portion which is elastically deformed by pivoting of the deflectable post towards the housing and wherein the third portion comprises a coil.

19. The spine stabilization device of claim 12, wherein the spring comprises one or more spring washers.

20. The spine stabilization device of claim 12, wherein the spring is radially compressed by deflection of the deflectable post.

21. The device of claim 12, wherein the spring includes a plurality of arms that extend perpendicularly to the post.

22. A dynamic spine stabilization device comprising:
a bone anchor having a housing and a longitudinal axis;
a cavity in the housing coaxial with the longitudinal axis;
a post received in the cavity;
the post having a retainer at a distal end and a mount at a proximal end;
the retainer being secured in a pocket of the cavity of the housing such that the post may pivot within the housing;
a spring positioned in the cavity of the housing between the post and the housing such that deflection of the retainer in a direction perpendicular to the longitudinal axis causes compression of the spring in a direction parallel to the longitudinal axis; and
wherein the spring applies a force upon the post pushing the post towards a position in which the post is coaxial with the longitudinal axis.

23. The device of claim 22, wherein said spring comprises a plurality of lever arms arranged in a circle.

24. The device of claim 22, wherein said spring comprises a plurality of planar spring elements.

25. The device of claim 22, wherein:
said housing comprises a limit surface which contacts the post upon deflection of said post a first amount from the position in which the longitudinal axis of the post is coaxial with the bone anchor; and
wherein further deflection of said post beyond said first amount requires a larger load per unit of deflection than deflection of said post up to said first amount.

* * * * *